United States Patent
Ghildyal et al.

(10) Patent No.: US 6,969,596 B2
(45) Date of Patent: Nov. 29, 2005

(54) POLYNUCLEOTIDE ENCODING A HUMAN RECEPTOR TYROSINE KINASE

(75) Inventors: Namit Ghildyal, Kennett Square, PA (US); Govindaswamy Panchamoorthy, Wilmington, DE (US)

(73) Assignee: AstraZeneca AB, Sodertalje (SE)

( * ) Notice: Subject to any disclaimer, the term of this patent is extended or adjusted under 35 U.S.C. 154(b) by 309 days.

(21) Appl. No.: 10/040,884

(22) Filed: Jan. 7, 2002

(65) Prior Publication Data

US 2003/0078222 A1 Apr. 24, 2003

Related U.S. Application Data

(63) Continuation of application No. 09/310,438, filed on May 12, 1999, now abandoned.
(60) Provisional application No. 60/088,958, filed on Jun. 11, 1998.

(51) Int. Cl.$^7$ .......................... C12N 15/12; C12N 5/10; C12N 15/63
(52) U.S. Cl. .................... 435/69.1; 435/71.1; 435/71.2; 435/325; 435/471; 435/320.1; 435/252.3; 435/254.11; 536/23.5
(58) Field of Search .............................. 435/69.1, 71.1, 435/71.2, 325, 471, 320.1, 252.3, 254.11; 536/23.5

(56) References Cited

U.S. PATENT DOCUMENTS

| | | | |
|---|---|---|---|
| 5,763,198 A | 6/1998 | Hirth et al. | 435/7.21 |
| 5,763,441 A | 6/1998 | App et al. | 514/249 |
| 5,763,470 A | 6/1998 | Tang et al. | 514/406 |
| 5,763,584 A | 6/1998 | Godowski | 530/402 |

FOREIGN PATENT DOCUMENTS

| | | |
|---|---|---|
| WO | WO 95/30331 | 11/1995 |
| WO | WO 97/34920 | 9/1997 |

OTHER PUBLICATIONS

Shawver et al., 1997, Receptor tyrosine kinases as targets for inhibition of angiogenesis, Drug Discovery Today, 2:50–63.
Herz et al., 1997, Molecular approaches to receptors as targets for drug discovery, J. Recept. Signal Transduct. Res., 17:671–776.
Marra et al., The WashU–HHMI mouse EST project, EMBL ACC NO AA098024, Oct. 27, 1996.
Auffray et al., IMAGE: integrated molecular analysis of the human genome and its expression, EMBL ACC NO Z42722, Nov. 6, 1994.
Rubin Grandis et al., Inhibition of epidermal growth factor receptor gene expression and function decreases proliferation of head and neck squamous carcinoma but not normal mucosal epithelial cells, Oncogene, 15:409–416.
Chou et al., 1987, Human insulin receptors mutated at the ATP–binding site lack protein tyrosine kinase activity and fail to mediate postreceptor effects of insulin, J. Bio. Chem., 262:1842–1847.
Mikayama et al., Molecular cloning and functional expression of a cDNA encoding glycosylation–inhibiting factor, Proc. Natl. Acad. Sci., 1993, pp. 10056–10060, vol. 90.
Voet et al., Biochemistry, pp. 126–128, 228–234, John Wiley & Sons, Inc. 1990.

*Primary Examiner*—Prema Mertz
(74) *Attorney, Agent, or Firm*—Robin S. Quartin

(57) ABSTRACT

An isolated and purified human receptor tyrosine kinase is described. A cDNA sequence which encodes the native polypeptide is disclosed as well as the structural coding region and the amino acid residue sequence of the tyrosine kinase. Methods are provided which employ novel sequences to identify compounds that modulate the biological and/or pharmacological activity of the tyrosine kinase and hence regulate cellular and tissue physiology. Biologically-effective antisense molecules, as well as dominant negative mutant versions of the kinase, are described which are suitable for therapeutic use. The invention is also related to the diagnosis, study, prevention, and treatment of pathophysiological disorders related to or mediated by the biological molecule.

4 Claims, No Drawings

SEQUENCE LISTING

<160> NUMBER OF SEQ ID NOS: 6

<210> SEQ ID NO 1
<211> LENGTH: 2607
<212> TYPE: DNA
<213> ORGANISM: Homo Sapiens

<400> SEQUENCE: 1

| | | | | | |
|---|---|---|---|---|---|
| gaggagggac | acggaattac | tcacagctgt | gctgtgtgca | ttctctgtgg | gcctagcagg | 60 |
| gaagggaca | gccctgtggc | aatgggcatg | acacggatgc | tcctggaatg | cagtctcagt | 120 |
| gacaagttgt | gtgtcatcca | ggagaagcag | tatgaagtga | ttatcgtccc | aactttgttg | 180 |
| gttactatct | tcctcatcct | tcttggggtc | atcctgtggc | tttttatcag | agaacaaaga | 240 |
| actcaacagc | agcgttctgg | acctcaaggc | attgcccctg | ttcctccacc | tagggaccta | 300 |
| agctgggaag | caggacatgg | aggaaatgtg | gctttgccac | ttaaggagac | atccgtggaa | 360 |
| aactttctgg | gagctaccac | acctgccctg | gctaagctgc | aggtgccgcg | ggagcaactc | 420 |
| tctgaagttc | tggagcagat | ttgcagtggt | agctgtgggc | ccatctttcg | agccaatatg | 480 |
| aacactgggg | acccttctaa | gcccaagagt | gttattctca | aggctttaaa | agaaccagct | 540 |
| gggctccatg | aggtacaaga | tttcttaggg | cgaatccaat | tccatcaata | cctggggaaa | 600 |
| cacaaaaacc | tggtgcagct | ggaaggctgc | tgcactgaaa | agctgccact | ctatatggtg | 660 |
| ttggaggatg | tggcccaggg | ggacctgctc | ggctttctct | ggacctgtcg | gcgggatgtg | 720 |
| atgactatgg | atggtcttct | ctatgatctc | acagaaaaac | aagtatatca | catcggaaag | 780 |
| caggtccttt | tggcgctgga | attcctgcag | gagaagcatt | tgttccatgg | ggatgtggca | 840 |
| gccaggaata | ttctgatgca | aagtgatctc | actgctaagc | tctgtggatt | aggcctggct | 900 |
| tatgaagttt | acacccgagg | ggccatctcc | tctactcaaa | ccatacctct | caagtggctt | 960 |
| gccccagaac | ggcttctcct | gagacctgct | agcatcagag | cagatgtctg | gtcttttggg | 1020 |
| atcctgctct | atgagatggt | gactctagga | gcaccaccgt | atcctgaagt | ccctcctacc | 1080 |
| agcatcctag | agcatctcca | aagaaggaaa | atcatgaaga | gacccagtag | ctgcacacat | 1140 |
| accatgtaca | gtatcatgaa | gtcctgctgg | cgctggcgtg | aggctgaccg | cccctcacct | 1200 |
| agagagctgc | gcttgcgcct | agaagctgcc | attaaaactg | cagatgacga | ggctgtgtta | 1260 |
| caagtaccag | agttggtggt | acctgaactg | tatgcagctg | tggccggcat | cagagtggag | 1320 |
| agcctcttct | acaactatag | catgctttga | agagtctcgg | gcaagaaaca | ttcatgcatg | 1380 |
| agtatatgtt | cttggaatca | attcctctaa | gaacagagaa | tggtctttcc | cagggacaca | 1440 |
| aagggagaaa | tgggacatgg | attcttgatc | ttcctttaca | catttctcgg | gaaatctgaa | 1500 |
| atgatgctgg | atgggactct | acacatcctg | agctaagaca | tactgtcagt | ctcacttctg | 1560 |
| ctgtcccagt | cctagaaatc | ctgggtagaa | gtggtggacc | tgtgcaaagg | aggttttaga | 1620 |

```
actctgcagt atttgttggg gcatggcaca aataagctca tccctcccgt ccgaggctag    1680
tttcctctgg aaccacattt ttatctagat gaaaatttgg aatgaaatga aggaatagaa    1740
atccaataaa agagttgaag ggaaagaaaa tttaaggttc ttcttgctca ggattacaga    1800
tatggaccaa cacctccttc aagaaaaggt ggtaggacac aaagttcttc agtcctgagc    1860
cctacatgtg gggctggagg agaactataa cggaaaaacc tctgagtttc accttaggta    1920
tagataaaag aaagatggtc ccctttatc tgattctgag acaggtaaat tctgtttgtt    1980
actacgttta attagaaggt ggaggagtca tttcatgatt aagaacattc aacatgtatt    2040
gttcattaag ctagcttcct agttccgatt agactaagga gactaagcct agagagtcaa    2100
tgttagaaca gtgaaaagaa ttctgtgtgt gtgtgtgtgt gtgtgtgtgt gtgcacaata    2160
aataggaaat gtgaaaacca agcaagaagg cttagtagct cagtctttaa caagggctag    2220
aaaagaatgt aatctgatat ggaaggatag cagcttctaa ttttcaatca tctgttgata    2280
tactgtgaaa cttattttat taaattaata tttattaaat ggaaatatgc ttttctggtt    2340
tataactact aaaaatatca tagggaggat aaaagtaaat aagtgaaagt taatgccaat    2400
agaaaaattc aagagataat gtacaatgtc agaaaaggga ttctttatgt gtaaatgggg    2460
ataataccta tttcacaagg ttgttytgag gattgatacg ttttgagtat gtatttgtac    2520
actatctggc acatatgcgc tcaataaacg tgtttctcct taaaaaaaaa aaaaaaaaa    2580 aaaaaaaaaa aaaaaaaaa aaaaaaa                                       2607

<210> SEQ ID NO 2
<211> LENGTH: 1269
<212> TYPE: DNA
<213> ORGANISM: Homo Sapiens

<400> SEQUENCE: 2
atgggcatga cacggatgct cctggaatgc agtctcagtg acaagttgtg tgtcatccag      60
gagaagcagt atgaagtgat tatcgtccca actttgttgg ttactatctt cctcatcctt    120 cttgggtca tcctgtggct ttttatcaga gaacaaagaa ctcaacagca gcgttctgga    180
cctcaaggca ttgcccctgt tcctccacct agggacctaa gctgggaagc aggacatgga    240
ggaaatgtgg ctttgccact taaggagaca tccgtggaaa actttctggg agctaccaca    300
cctgccctgg ctaagctgca ggtgccgcgg agcaactct ctgaagttct ggagcagatt    360
tgcagtggta gctgtgggcc catctttcga gccaatatga acactgggga cccttctaag    420
cccaagagtg ttattctcaa ggctttaaaa gaaccagctg ggctccatga ggtacaagat    480
ttcttagggc gaatccaatt ccatcaatac ctggggaaac acaaaaacct ggtgcagctg    540
gaaggctgct gcactgaaaa gctgccactc tatatggtgt tggaggatgt ggcccagggg    600
gacctgctcg gctttctctg gacctgtcgg cgggatgtga tgactatgga tggtcttctc    660
tatgatctca cagaaaaaca agtatatcac atcggaaagc aggtcctttt ggcgctggaa    720
ttcctgcagg agaagcattt gttccatggg gatgtggcag ccaggaatat tctgatgcaa    780
agtgatctca ctgctaagct ctgtggatta ggcctggctt atgaagttta cacccgaggg    840
gccatctcct ctactcaaac catacctctc aagtggcttg ccccagaacg gcttctcctg    900
agacctgcta gcatcagagc agatgtctgg tcttttggga tcctgctcta tgagatggtg    960
actctaggag caccaccgta tcctgaagtc cctcctacca gcatcctaga gcatctccaa   1020
agaaggaaaa tcatgaagag acccagtagc tgcacacata ccatgtacag tatcatgaag   1080
tcctgctggg gctggcgtga ggctgaccgc ccctcaccta gagagctgcg cttgcgccta   1140
```

-continued

```
gaagctgcca ttaaaactgc agatgacgag gctgtgttac aagtaccaga gttggtggta    1200
cctgaactgt atgcagctgt ggccggcatc agagtggaga gcctcttcta caactatagc    1260
atgctttga                                                            1269
```

<210> SEQ ID NO 3
<211> LENGTH: 422
<212> TYPE: PRT
<213> ORGANISM: Homo Sapiens

<400> SEQUENCE: 3

```
Met Gly Met Thr Arg Met Leu Leu Glu Cys Ser Leu Ser Asp Lys Leu
  1               5                  10                  15

Cys Val Ile Gln Glu Lys Gln Tyr Glu Val Ile Ile Val Pro Thr Leu
                 20                  25                  30

Leu Val Thr Ile Phe Leu Ile Leu Leu Gly Val Ile Leu Trp Leu Phe
             35                  40                  45

Ile Arg Glu Gln Arg Thr Gln Gln Arg Ser Gly Pro Gln Gly Ile
 50                  55                  60

Ala Pro Val Pro Pro Arg Asp Leu Ser Trp Glu Ala Gly His Gly
 65                  70                  75                  80

Gly Asn Val Ala Leu Pro Leu Lys Glu Thr Ser Val Glu Asn Phe Leu
                 85                  90                  95

Gly Ala Thr Thr Pro Ala Leu Ala Lys Leu Gln Val Pro Arg Glu Gln
                100                 105                 110

Leu Ser Glu Val Leu Glu Gln Ile Cys Ser Gly Ser Cys Gly Pro Ile
            115                 120                 125

Phe Arg Ala Asn Met Asn Thr Gly Asp Pro Ser Lys Pro Lys Ser Val
130                 135                 140

Ile Leu Lys Ala Leu Lys Glu Pro Ala Gly Leu His Glu Val Gln Asp
145                 150                 155                 160

Phe Leu Gly Arg Ile Gln Phe His Gln Tyr Leu Gly Lys His Lys Asn
                165                 170                 175

Leu Val Gln Leu Glu Gly Cys Cys Thr Glu Lys Leu Pro Leu Tyr Met
            180                 185                 190

Val Leu Glu Asp Val Ala Gln Gly Asp Leu Gly Phe Leu Trp Thr
            195                 200                 205

Cys Arg Arg Asp Val Met Thr Met Asp Gly Leu Leu Tyr Asp Leu Thr
210                 215                 220

Glu Lys Gln Val Tyr His Ile Gly Lys Gln Val Leu Ala Leu Glu
225                 230                 235                 240

Phe Leu Gln Glu Lys His Leu Phe His Gly Asp Val Ala Ala Arg Asn
                245                 250                 255

Ile Leu Met Gln Ser Asp Leu Thr Ala Lys Leu Cys Gly Leu Gly Leu
            260                 265                 270

Ala Tyr Glu Val Tyr Thr Arg Gly Ala Ile Ser Ser Thr Gln Thr Ile
            275                 280                 285

Pro Leu Lys Trp Leu Ala Pro Glu Arg Leu Leu Arg Pro Ala Ser
290                 295                 300

Ile Arg Ala Asp Val Trp Ser Phe Gly Ile Leu Leu Tyr Glu Met Val
305                 310                 315                 320

Thr Leu Gly Ala Pro Pro Tyr Pro Glu Val Pro Pro Thr Ser Ile Leu
                325                 330                 335

Glu His Leu Gln Arg Arg Lys Ile Met Lys Arg Pro Ser Ser Cys Thr
```

-continued

```
              340                 345                 350
His Thr Met Tyr Ser Ile Met Lys Ser Cys Trp Arg Trp Arg Glu Ala
        355                 360                 365

Asp Arg Pro Ser Pro Arg Glu Leu Arg Leu Arg Leu Glu Ala Ala Ile
    370                 375                 380

Lys Thr Ala Asp Glu Ala Val Leu Gln Val Pro Glu Leu Val Val
385                 390                 395                 400

Pro Glu Leu Tyr Ala Ala Val Ala Gly Ile Arg Val Glu Ser Leu Phe
                405                 410                 415

Tyr Asn Tyr Ser Met Leu
                420

<210> SEQ ID NO 4
<211> LENGTH: 15
<212> TYPE: PRT
<213> ORGANISM: Homo Sapiens

<400> SEQUENCE: 4

Glu Ala Asp Arg Pro Ser Pro Arg Glu Leu Arg Leu Arg Leu Glu
1               5                   10                  15

<210> SEQ ID NO 5
<211> LENGTH: 27
<212> TYPE: DNA
<213> ORGANISM: Artificial Sequence
<220> FEATURE:
<223> OTHER INFORMATION: PCR Primer

<400> SEQUENCE: 5
gccgtcgact gtgggcctag cagggaa                                    27

<210> SEQ ID NO 6
<211> LENGTH: 27
<212> TYPE: DNA
<213> ORGANISM: Artificial Sequence
<220> FEATURE:
<223> OTHER INFORMATION: PCR Primer

<400> SEQUENCE: 6
gccgcggccg ctcaaagcat gctatag                                    27
```

POLYNUCLEOTIDE ENCODING A HUMAN RECEPTOR TYROSINE KINASE

CROSS-REFERENCE TO RELATED APPLICATIONS

This application is a continuation of U.S. patent application Ser. No. 09/310,438, filed May 12, 1999, now abandoned, which claimed benefit under 35 U.S.C. §119(e) of U.S. Provisional Application No. 60/088,958, filed Jun. 11, 1998. All applications are hereby incorporated herein by reference in their entireties.

FIELD OF THE INVENTION

The present invention relates to nucleic acid and amino acid sequences pertaining to a novel receptor tyrosine kinase and to the use of these sequences to identify compounds that modulate a biological and/or pharmacological activity of the native biomolecule. The invention also relates to biologically-effective antisense molecules, as well as dominant negative mutant versions of the receptor tyrosine kinase which are suitable for therapeutic use. The invention is also related to the diagnosis, study, prevention, and treatment of pathophysiological disorders related to or mediated by the receptor tyrosine kinase.

BACKGROUND OF THE INVENTION

Pathologic angiogenesis occurs under many conditions and is thought to be induced by local ischemia. Diseases in which angiogenesis is thought to play a critical role in the underlying pathology include: ocular diseases such as diabetic retinopathy, retinopathy or prematurity and age-related macular degeneration; vascular diseases such as ischemic heart disease and atherosclerosis; chronic inflammatory disorders such as psoriasis and rheumatoid arthritis; and solid tumor growth. A recent review primarily focuses on the role or RTKs in tumor angiogenesis. Shawver, L. K., et al., *Receptor Tyrosine Kinases as Targets for Inhibition of Angiogenesis*, Drug Discovery Today (Elsevier Science Ltd.), 2(2):50 (1997). The review primarily addresses the role of growth factors and their receptor tyrosine kinases (RTKs) in the regulation of microvessel physiology as they relate to the angiogenic process. New blood vessel growth is required for the growth and metastasis of solid tumors. The significance of angiogenesis in human tumors has been highlighted by recent studies that relate the angiogenic phenotype to patient survival. These studies found that the number of microvessels in a primary tumor has prognostic significance in breast carcinoma, bladder carcinomas, colon carcinomas and tumors of the oral cavity. Anti-angiogenic agents potentially have broad applications in the clinic. Id. See, also, Herz, Jeffrey M., et al., *Molecular Approaches to Receptors as Targets for Drug Discovery*, J. of Receptor & Signal Transduction Research, 17(5):671 (1997).

RTKs (also known as growth factor receptors) play an important role in many cellular processes. All of these molecules have an extracellular ligand-binding domain. Upon ligand binding, receptors dimerize, the tyrosine kinase is activated and the receptors become autophosphorylated. Ulrich, A., et al., Cell, 61:203 (1990). The cascade triggered by RTK activation modulates cellular events, determining proliferation, differentiation and morphogenesis in a positive or negative fashion. Disturbances in the expression of growth factors, their cognate RTKs, or constituents of downstream signaling pathways are commonly associated with many types of cancer. Gene mutations giving rise to altered protein products have been shown to alter the regulatory mechanisms influencing cellular proliferation, resulting in tumor initiation and progression. Shawver, L. K., et al., *Receptor Tyrosine Kinases as Targets for Inhibition of Angiogenesis*, DDT (Elsevier Science Ltd.), 2(2):50 (1997).

One strategy for interfering with receptor signaling is to inhibit ligand binding. This can be accomplished with specific receptor-binding antagonists such as ligand fragments, or with nonspecific antagonists such as suramin, with neutralizing antibodies to either the ligand or receptor, or with an excess of soluble receptor or ligand-binding protein, which will sequester the ligand. A second strategy for interfering with receptor signaling is to block signal transduction by overexpression of a dominant-negative receptor. Because receptor kinases typically dimerize to induce signal transduction through transphosphorylation, prevention of receptor dimerization due to overexpression of kinase-deficient receptors will attenuate activation of signaling. Receptors can be made kinase-deficient by introduction of a point mutation in amino acids critical for kinase function, or deletion of the kinase or entire cytoplastic domain. Another strategy for understanding receptor function involves depleting the receptor protein. This can be accomplished by the introduction of exogenous agents such as antisense oligonucleotides, antisense RNA, or ribozymes, all of which lead to degradation of the receptor mRNA and gradual depletion of the protein in the cell. Id.

The profound cellular effects mediated by tyrosine kinases and phosphotyrosine phosphatases have made them attractive targets for the development of new therapeutic molecules. It is known, for example, that the overexpression of tyrosine kinases, such as HER2, can play a decisive role in the development of cancer and that antibodies capable of blocking the activity of this enzyme can abrogate tumor growth. Slamon, D. J., et al., Science, 235:177 (1987); Drebin, et al., Oncogene 2:387 (1988). More recently, attempts have been made to identify small molecules which act as tyrosine kinase inhibitors. For example, bis monocyclic, bicyclic or heterocyclic aryl compounds (PCT WO 92/20642), vinylene-azaindole derivatives (PCT WO 94/14808) and 1-cyclopropyl-4-pyridyl-quinolones (U.S. Pat. No. 5,330,992) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0 566 266 A1), seleoindoles and selenides (PCT WO 94/03427), tricyclic polyhydroxylic compounds (PCT WO 92/21660) and benzylphosphonic acid compounds (PCT WO 91/15495) have been described as compounds for use as tyrosine kinase inhibitors for use in the treatment of cancer.

The availability of a novel human receptor tyrosine kinase species which is clearly implicated by a functional connection to disease will be ideal for such drug screening as well as diagnosis, study, prevention, and treatment of pathophysiological disorders related to the biological molecule.

SUMMARY OF THE INVENTION

The present invention is directed to a purified polynucleotide comprising a nucleic acid sequence which encodes a peptide having at least about 80% homology to a member selected from the group consisting essentially of: (SEQ ID NO:3, SEQ ID NO:3 positions 1–25, SEQ ID NO:3 positions 1–122, SEQ ID NO:3 positions 26–422, and SEQ ID NO:3 positions 123–422).

The present invention is also directed to a purified polynucleotide comprising a nucleic acid sequence which encodes a polypeptide comprising the sequence as depicted in SEQ ID NO:3 wherein position 147 (Lysine) of SEQ ID NO:3 is substituted or deleted.

Isolated and purified polynucleotides of the present invention include but are not limited to sequences comprising SEQ ID NO: 1 and SEQ ID NO:2.

The current invention is directed to a purified polypeptide comprising the amino acid sequence as depicted in SEQ ID NO:3 or a variant of SEQ ID NO:3 having at least about 80% homology to a member selected from the group consisting essentially of: (SEQ ID NO:3, SEQ ID NO:3 positions 1–25, SEQ ID NO:3 positions 1–122, SEQ ID NO:3 positions 26–422, and SEQ ID NO:3 positions 123–422).

A preferred embodiment of the invention is an isolated and purified biologically effective antisense polynucleotide molecule comprising an oligomer in the range from about 12 to about 25 nucleotides in length which is complementary to a region within positions 67–148 and 1333–1414 of SEQ ID NO:1.

The invention is further directed to an expression vector, as well as host cells which harbor the expression vector, for the expression of a polypeptide, wherein said vector comprises a nucleic acid sequence which encodes a polypeptide as depicted in SEQ ID NO:3 or a pharmacologically and/or biologically active or biologically effective derivative thereof.

The instant invention is further directed to methods of identifying compounds that modulate a biological and/or pharmacological activity of a tyrosine kinase, which comprise:
(a) combining a candidate compound modulator of activity with a polypeptide having the sequence as depicted in SEQ ID NO:3 or a variant thereof, and
(b) measuring an effect of the candidate compound modulator on the biological and/or pharmacological activity of the polypeptide.

The present invention is also directed to compounds identified by means of methods provided wherein said compound modulates the biological and/or pharmacological activity of a tyrosine kinase.

Additionally, the invention is directed to methods of treatment of a patient in need of such treatment for a condition which is mediated by a tyrosine kinase, comprising administering: (a) an effective amount of a compound identified by means of provided methods; and/or (b) an effective amount of a polynucleotide which encodes a biologically effective dominant negative mutant polypeptide comprising the sequence as depicted in SEQ ID NO:3 or a contemplated variant thereof; and/or (c) an effective amount of a biologically effective antisense molecule derived from the complement of SEQ ID NO: 1.

DETAILED DESCRIPTION OF THE INVENTION

Unless defined otherwise, all technical and scientific terms used herein have the same meaning as is commonly understood by one of skill in the art to which this invention belongs. All publications and patents referred to herein are incorporated by reference.

Biological activity as used herein in reference to the tyrosine kinase of the present invention refers to the kinase activity of the biomolecule and/or to the performance of any one or more of the functions including but not limited to the ability to autophosphorylate, to phosphorylate a substrate, to bind ATP, and to mediate the activation of Cdc2 kinase.

Pharmacological activity as used herein in reference to the tyrosine kinase of the present invention refers to the direct or indirect transcriptional activation of one or more genes; as well as the ability to mediate any one or more of the physiological conditions including but not limited to mitosis, cell differentiation, proliferation, oncogenic transformation, neoplasia, macrophage regulation, endothelial cell regulation, fibroblast regulation, cytoskeletal structure, metastases, cell aggregation, cell motility, cytokinesis, cancer, angiogenesis, cell senescence, acute and chronic inflammation, auto-immune disorders, arthritis, neurogenerative processes, allergic response, stress response, secretion, apoptosis, cachexia, neurological disorders, peripheral vascular disease, atherosclerosis, heart disease, asthma, and atheroma.

Dominant negative mutant as used herein refers to a polypeptide or a nucleic acid coding region sequence which has been changed with regard to at least one position in the sequence, relative to the corresponding wild type native version at a position which changes an amino acid residue position at an active site required for biological and/or pharmacological activity of the native peptide. Dominant negative mutants of SEQ ID NO:3 contemplated herein include, but are not limited to, polypeptide species which manifest any change with regard to any change in the residue Lys(K)$^{147}$.

Biologically effective as used herein in reference to antisense nucleic acid molecules as well as dominant negative mutant nucleic acid coding regions and dominant negative mutant peptides refers to the ability of these molecules to modulate the biological and/or pharmacological activity of the tyrosine kinase of the present invention, including direct or indirect modulation of transcriptional activation of one or more genes, and/or transcription/translation of nucleic acid coding regions of the tyrosine kinase of the present invention. Biologically effective antisense molecules as well as nucleic acids which encode biologically effective dominant negative mutant versions of SEQ ID NO:3, or derivatives thereof, are preferred embodiments of the present invention.

As depicted as used herein refers the sequence as well as inherent derivatives thereof, e.g., functional derivative that demonstrate or perform substantially the same biological and/or pharmacological activity in substantially the same way. 'As depicted' is therefore intended to encompass biologically and/or pharmacologically active truncated versions clearly derived from the sequences disclosed and characterized herein (e.g., evidenced domains) as well as chimeric sequences which contain one or more of them.

Variant as used herein refers to sequences substantially as shown having changes, e.g., a polypeptide sequence comprising a sequence which differs from the sequence referred to by at least one amino acid substitution, addition, or deletion, preferrably a conservative amino acid substitution, that demonstrate or perform substantially the same biological and/or pharmacological activity in substantially the same way, as well as truncated versions of these variants. However, variant as used herein is intended to encompass all contemplated biologically effective dominant negative mutants, several species of which are set forth herein.

The term modulation is used herein to refer to the capacity to either enhance or inhibit a function of a biological molecule including, but not limited to, a biological and/or pharmacological activity of a tyrosine kinase molecule, or to the capacity to either enhance or inhibit a functional property of a nucleic acid coding region. Modulate physiology as used herein refers to the biophysiological regulation of cells and/or tissue and the treatment of pathophysiological disorders related thereto.

Direct administration as used herein refers to the direct administration of nucleic acid molecules, peptides, or compounds as well as contemplated derivatives/variants of the present invention. Direct administration includes but is not limited to ex vivo as well as in vivo gene therapy techniques.

Purified as used herein refers to molecules, either nucleic acid or amino acid sequences, that are removed from their natural environment and isolated or separated from at least one other component with which they are naturally associated.

Expression vector as used herein refers to nucleic acid vector constructions to direct the transcription of nucleic acid regions in host cells. Expression vectors include but are not limited to plasmids, retroviral vectors, viral and synthetic vectors.

Transformed host cells as used herein refer to cells which harbor one or more nucleic acids of the present invention.

RTKs

A wide variety of polypeptide growth factor receptors that possess intrinsic tyrosine kinase activity have now been characterized. Activated receptor tyrosine-kinases (RTKs) undergo dimerization and initiate signaling through tyrosine-specific phosphorylation of diverse intermediates, activating a cascade of intracellular pathways that regulate phospholipid and arachidonate metabolism, calcium mobilization, protein phosphorylation (involving other protein kinases), and transcription regulation. The growth factor-dependent tyrosine kinase activity of the RTK cytoplasmic domain is the primary mechanism for generation of intracellular signals that initiate multiple cellular responses. Cellular responses mediated by RTKs include alterations in gene expression, cell proliferation, cytoskeletal architecture, cell metabolism, differentiation and cell survival. Receptor-tyrosine kinases consist of an amino-terminal extracellular ligand binding domain, a transmembrane domain, and a carboxyl-terminal intracellular tyrosine kinase domain. Herz, Jeffrey M., et al., *Molecular Approaches to Receptors as Targets for Drug Discovery*, J. of Receptor & Signal Transduction Research, 17(5):671 (1997).

Although there is a tremendous diversity among the numerous members of the RTK family, the signaling mechanisms used by these receptors share many common features. Biochemical and molecular genetic studies have shown that binding of the ligand to the extracellular domain of the RTK rapidly activates the intrinsic tyrosine kinase catalytic activity of the intracellular domain. Enzymatic activity of the RTK kinase domain is essential for signal transduction. The increased activity also leads to phosphorylation of a number of intracellular substrates and activation of numerous downstream signaling molecules. Examples of proteins that are frequently activated include: phospholipase-C-γ (PLC-γ), phosphatidylinositol 3-kinase (PI-3kinase), GTPase activating protein, $pp60^{c-arc}$ protein tyrosine kinase, p21-ras and others. Id.

The role of receptor tyrosine kinases (RTKs) in the formation of new blood vasculature associated with human disease has provided a strong rationale to identify ways of inhibiting the function of these enzymes. The vast majority of efforts have focused on the inhibition of FGF and VEGF receptors. Other RTKs have been implicated in angiogenesis. These targets would be amenable to many of the approaches that have been taken using the FGF and VEGF receptor targets. The therapeutic modalities that have been studied for abrogation of FGF- and VEGF-dependent signaling include the use of nucleotides (gene therapy and antisense), proteins, (antibodies, receptor and ligand decoys) low-molecular-weight compounds, as well as expression of a dominant-negative forms. The use of low-molecular-weight compounds to treat angiogenesis represents an ever-expanding area of research activities. Shawver, L. K., et al., *Receptor Tyrosine Kinases as Targets for Inhibition of Angiogenesis*, DDT (Elsevier Science Ltd.), 2(2):50 (1997).

Rheumatoid arthritis, although characterized by inflammation and immunoproliferation, is another disease in which angiogenesis has been implicated in the disease process because RTKs represent proteins with enzymatic function, they lend themselves to a pharmacological intervention with small-molecule compounds. Id.

Human Receptor Tyrosine Kinase

A 2607 base pair cDNA sequence, SEQ ID NO: 1, which pertains to the human receptor tyrosine kinase SEQ ID NO:3 is set forth herein. The 1269 base pair structural region, ATG to TGA, SEQ ID NO:2, which encodes SEQ ID NO:3 (422 amino acids), is contained in SEQ ID NO: 1.

The physical sequence (SEQ ID NO:3) contains all of the tyrosine kinase signature sequences, juxtamembrane sequences, transmembrane sequences and extracellular sequences that show structural similarity to the known receptor tyrosine kinases, e.g., FGF-R, EGF-R, PDGF-R, IGF-R, VEGF-R, FLK, FLT, TIE, as well as others known in the art. See, e.g., Dionne, C. A., et al., EMBO, 9:2685 (1990); Berchuck, A., et al., Am. J. Obstet. Gynecol., 161:1247 (1989); Kraus, M. H., et al., Ann. NY Acad. Sci.,551:320 (1988); Bishop, J. M., et al., Science, 235:305 (1987). SEQ ID NO:3 demonstrates attributes of the polypeptide which include a 24-residue transmembrane domain which separates an extracellular portion from the cytoplasmic domain. The cytoplasmic domain includes a juxtamembrane sequence immediately followed by the tyrosine kinase domain containing eleven subdomains. The signature sequences demonstrated in the novel human receptor tyrosine kinase signal transduction molecule (SEQ ID NO:3) are each of the Subdomains I-XI.

The role of receptor tyrosine kinases in cellular proliferation, inter alia, has led to the belief that RTKs have significant roles in mediation of disease and accordingly have significant potential as specific therapeutic targets. Accordingly, modulating agents of specific RTK kinase activity and/or receptor activity are highly sought after in the pharmaceutical industry as candidate development compounds. Receptor Tyrosine Kinase molecules that are particularly characteristic of disease tissue, e.g., adenocarcinoma, (e.g., SEQ ID NO:3) serve as paramount candidates toward diagnosis of disease conditions as well as targets for modulation of tissue physiology.

SEQ ID NO: 1 has been mapped to chromosome 12p12.3 using Stanford G3 radiation hybrid panel by means of of cell clones obtained from Research Genetics, Huntsville, Ala. Stewart et al., Genome Res., 7, 422 (1997). Cytogenetic abnormalities and loss of heterozygosity 12p12 have been shown to occur in a large number of tumor types in addition to adenocarcinomas e.g. germ cell tumors, oral SCC, ovarian Ca, acute lymphocytic leukemia, and testicular germ cell tumors. Chromosome 12p12-p13 region has been shown to be amplified (4–11 copies) in a large number of tumors.

SEQ ID NO:1 demonstrates a total of 14 GT repeat sequences between positions 2125 and 2152. DNA sequencing of the corresponding genomic DNA from 27 unrelated Caucasians showed 11,12,13,14 and 15 copies of the GT repeat in the tyrosine kinase gene corresponding to SEQ ID NO: 1 from 27 caucasians with the following respective frequencies: 6/54; 2/54; 17/54; 16/54; and 13/54. No homozygotes were observed for any allele. This variable number CA/GT repeat can be used as a genetic marker for the receptor tyrosine kinase gene and for the chromosomal 12p12.3 for both disease association studies or loss of heterozygosity studies. Each of these alleles is intended to be within the scope of the claims appended hereto (e.g., PCR primers which can readily be constructed therefrom by a person of ordinary skill for diagnostic methods and/or compositions). See, Example II.

Messenger RNA Pertaining to SEQ ID NO:1 is Selectively Expressed in Human Forebrain Northern Blots obtained from Clontech (Palo Alto, Calif.) showed that one or more genes pertaining to the novel tyrosine kinase (SEQ ID NO:1) was selectively transcribed in human forebrain tissue. High expression levels mRNA pertaining to the receptor tyrosine kinase were observed in the putamen and frontal lobe, in contrast to low to undetectable levels of transcript in cerebellum and medulla tissue.

SEQ ID NO:3 is Overexpressed in a Large Number of Tumors and Within the Brain Tissues of Alzheimer Patients In collaboration with LifeSpan Biosciences (Seattle, Wash.) an immunocytochemical analysis was conducted by the employment of primary clinical samples and the antibody described herein. In normal tissues, the anti-SEQ ID NO:3 antibody demonstrates positive staining: in occasional neurons and glial cells and less frequently in their cell processes, within epithelium of the breast, the enterocytes and Schwann cells within the colon, APUD cells, hepatocytes and kupffer cells, occasional Type 2 pneumocytes, and within macrophages, polymorphonucleur leukocytes, and a subset of lymphocytes, plasma cells and endothelial cells. The staining is negative in normal cell types including fibroblasts, adipocytes, goblet cells, the smooth muscle of the muscularis mucosa and muscularis propria, bile ducts, Type I pneumocytes, respiratory epithelium lining bronchioles, and prostatic glandular epithelium.

| TISSUE | DIAGNOSIS | AGE/SEX |
| --- | --- | --- |
| Brain | Normal | 56/M |
| Brain | Normal | 45/F |
| Breast | Normal | 37/F |
| Breast | Normal | 69/F |
| Colon | Normal | 87/M |
| Colo-rectal | Normal | NA |
| Liver | Normal | 46/M |
| Liver | Normal | 75/M |
| Lung | Normal | ADULT |
| Lung | Normal | ADULT |
| Prostate | Normal | 75/M |
| Prostate | Normal | 46/M |
| Brain | Alzheimer's | 90/F |
| Brain | Alzheimer's | 81/M |
| Brain | Alzheimer's | 76/F |
| Brain | Alzheimer's | 80/F |
| Brain | Alzheimer's | 60/F |
| Brain | Glioblastoma | 52/M |
| Brain | Glioblastoma | 44/M |
| Brain | Metastatic adenocarcinoma | 70/M |
| Brain | Metastatic adenocarcinoma | 49/M |
| Breast | Mucinous adenocarcinoma | |
| Breast | Infiltrating ductal carcinoma | |
| Breast | Infiltrating ductal carcinoma | |
| Breast | Infiltrating ductal carcinoma | |
| Breast | Infiltrating ductal carcinoma | |
| Colon | Well differentiated adenocarcinoma | 89/M |
| Colon | Well differentiated adenocarcinoma | 62/M |
| Colon | Well differentiated adenocarcinoma | 77/M |
| Colon | Well differentiated adenocarcinoma | 87/M |
| Rectum | Well differentiated adenocarcinoma | ADULT |
| Rectum | Well differentiated adenocarcinoma | ADULT |
| Rectum | Well differentiated adenocarcinoma | ADULT |
| Rectum | Well differentiated adenocarcinoma | ADULT |
| Rectum | Well differentiated adenocarcinoma | ADULT |
| Prostate | Adenocarcinoma | |
| Prostate | Poorly differentiated adenocarcinoma | |
| Prostate | Adenocarcinoma | |
| Prostate | Adenocarcinoma | |
| Prostate | Adenocarcinoma | |
| Lung | Adenocarcinoma, large cell poorly differentiated | 53/F |
| Lung | Adenocarcinoma | 65/M |
| Liver | Hepatocellular carcinoma | 66/M |
| Liver | Hepatocellular carcinoma | 82/M |

Immunocytochemical Analysis of Diseased Tissues (Anti-SEQ ID NO:3 Antibody)

A. Cancer Tissues: Within neoplastic tissues, positive staining is demonstrated within two metastatic adenocarcinomas, positive staining within the five breast adenocarcinomas, positive staining within the five colon adenocarcinomas, positive staining within the five rectosigmoid adenocarcinomas, and positive staining within four of five prostatic adenocarcinomas, and three of five lung adenocarcinomas.

B. Alzheimer's Tissues: The most dramatic staining with the anti receptor tyrosine kinase antibody was seen within Alzheimer's cases, both those with and without evidence of additional ischemic injury (i.e., evidence of recent or old infarct due to thromboembolism). The degree of staining within the neurons in the brain tissue and glial cells of relatively normal areas was faint, and similar to the faint occasional staining of cells and cell processes seen within the normal brains. In contrast to the faint staining within normal regions, there was a significantly increased level of signal in neurons and their associated cell processes in areas of injury. In addition, this increase in signal was not marked within the cell processes of the neuropil (rather than in the perinuclear cytoplasm of the neuron or astrocyte), producing halo-like rings in a perisomatic distribution around neurons, arborizing signals around astrocytes, and extensive, scattered deposits within the axons and cell processes of the neuropil. The increase in signal was seen within brains without artifacts with significant alzheimer's (particularly in regions with a heavy concentration of neuritic plaques or neurofibrillary tangles), and also in brains that contained regions of infarct in addition to the classic changes of Alzheimer's disease.

SEQ ID NO:3 Tyrosine Kinase is Prominent in Prostate Cancer Tissue

Based on the immunohistochemical findings (supra) prostate tumor tissues were obtained from the National Disease Research Interchange, Phila., Pa. Western blot analysis of the tissue lysates confirmed the presence of two proteins (60 and 55 kDa) that reacted with the anti-SEQ ID NO:3 antibody. To further confirm whether these proteins are tyrosine phosphorylated, the prostate tumor sample was probed with anti-phosphotyrosine antibody. The anti-pY Ab bound to the 55 kDa protein (most prominent of all pY reacting proteins) in the prostate lysates which was found to be SEQ ID NO:3 upon stripping and re-probing the blot with anti-SEQ ID NO:3 antibody.

Antisense Oligonucleotides Derived from SEQ ID NO:1 Inhibit Proliferation of A549 Cells In view of the demonstration that the receptor tyrosine kinase is over expressed in tumor cell lines as well as primary clinical tumor tissues, pharmacological activity of the tyrosine kinase to induce cell proliferation was examined. Particularly we decided to investigate if antisense molecules complementary to regions of the receptor tyrosine kinase mRNA would have an effect on cell proliferation. Two example antisense oligonucleotides and their corresponding sense oligonucleotides (as controls) were synthesized which pertain to SEQ ID NO:1 positions 75–92 (oligo 1) and 1348–1365 (oligo 2) (further preferred embodiments of antisense molecules are set forth infra). The results of three independent experiments showed an average of 50% inhibition of A549 cell proliferation upon administration of antisense oligo 1. Administration of antisense oligo 2 demonstrated a 20% inhibitory effect. Each of the corresponding sense oligonucleotides (controls) demonstrated no effect upon proliferation. See Example III.

Biological Activity Studies using CD8 Chimeric Constructs

To verify a particular biological activity of the receptor tyrosine kinase, chimeric constructs were generated comprised of the CD8 extracellular domain (CD8 is a well-known CTL specific cell surface protein) and the cytoplasmic domain of SEQ ID NO:3 (positions 26–422). These constructs were successfully expressed in COS-7 cells, NIH/3T3 fibroblasts and HEK293 cell lines as determined by western blotting using the anti-SEQ ID NO:3 antibody. It has been reported that the extracellular Cys residues of CD8 can form intermolecular disulfide bonds, accordingly it was hypothesized that the chimeric molecules would dimerize, after expression, bringing the two kinase domains together and stimulating trans-phosphorylation. An in vitro kinase assay was performed on the immunoprecipitated material obtained from transfected HEK293 cells. The results showed that low levels of tyrosine phosphorylation was observed on the chimeric proteins. To further understand the cellular function of the receptor tyrosine kinase, a preliminary experiment was conducted in U937 cells transfected with the chimeras followed by the activation with anti-CD8 Ab for 15 min (U937 cells were chosen as they are non-adherent cells and hence require low amounts of anti-CD8 Ab). Results were analyzed by western blot analysis using anti-phosphotyrosine (pY) Ab. While there were subtle differences in the pY patterns between the Ab activated and inactivated lanes, a prominent tyrosine phosphorylated 34 kDa protein was found to show a retarded mobility in the anti-CD8 Ab activated sample. This 34 kDa protein was identified as Cdc2 upon re-probing the blot with anti-Cdc2 monoclonal Ab. This data clearly suggests that the the novel receptor tyrosine kinase (SEQ ID NO:3) is linked to cell cycle progression.

Biological activity as used herein in reference to the tyrosine kinase of the present invention refers inter alia to mediation of the activation of Cdc2 kinase which, in turn mediates mitosis. See, e.g., Nishio K., et al., Antitumor effects of butyrolactone I, a selective cdc2 kinase inhibitor, on human lung cancer cell lines, Anticancer Research, 16(6B):3387 (1996); Vincent I., et al., Aberrant expression of mitotic cdc2/cyclin B1 kinase in degenerating neurons of Alzheimer's disease brain, Journal of Neuroscience, 17(10):3588 (1997).

Expression of the Receptor Tyrosine Kinase During Nerve Growth Factor (NGF) Withdrawal in PC12 Cells Neuronal apoptosis as manifested in Alzheimer's disease is reported to be due in part to a non-dividing cell's uncoordinated attempt to reenter and progress through the cell cycle. Davis P K, et al., Journal of Neurochemistry, 68:2338 (1997). This is believed to be relevant to the fact that the receptor tyrosine kinase described herein is over expressed in tissue pertaining to both Alzheimer's disease as well as in proliferating primary tumors; as well the demonstration that activation of SEQ ID NO:3 is linked to cell cycle progression. As a corollary, it was decided to determine whether the novel tyrosine kinase is over expressed in apoptotic neuronal cells. Others have demonstrated that the level of Cdc2 kinase increases fivefold in apoptotic PC12 cells after NGF deprivation. Id. PC12 cells were treated with NGF for 10 days. The cells were then washed in medium and incubated in the absence of NGF for one hour. Cells were harvested and lysates subjected to SDS-PAGE electrophoresis followed by Western blotting with an anti-SEQ ID NO:3 antibody. Results demonstrated that SEQ ID NO:3 protein was dramatically upregulated 1 hour after NGF withdrawal. These data suggest that expression of SEQ ID NO:3 may be involved in neuronal apoptosis.

Pharmacological Significance

The receptor tyrosine kinase described herein (SEQ ID NO:3) is highly likely to be an important regulator of cellular growth in particular tumors. Similar to the EGFR family of RTK's (EGF-R, FGF-R, PDGF-R, Flk-1/KDR, Flt-1, Tie-1 and Tek/Tie-2), the novel human signal transduction tyrosine kinase is over expressed in a variety of carcinomas (e.g., colorectal adenocarcinoma and lung carcinoma) and appears to be intimitely related to, and may directly contribute to, malignant tumor development. Thus, identification of modulation agents are contemplated for treatment of a variety of adenocarcinomas.

Compounds (e.g., small-molecules, peptides, analogs, mimetics) that modulate the pharmacological and/or biological activity of the receptor tyrosine kinase described herein are contemplated for use in the treatment of a wide variey of disease conditions including, but not limited to disease manifested by abnormal angiogenesis, peripheral vascular disease, arthritis, ocular diseases such as diabetic retinopathy, retinopathy or prematurity and age-related macular degeneration, ischemic heart disease and atherosclerosis, chronic inflammatory disorders such as psoriasis and rheumatoid arthritis; and solid tumor growth and metastasis.

SEQ ID NO:3, or nucleic acid sequences coding therefor, e.g. SEQ ID NO:1 and/or SEQ ID NO:2, have significant potential for the ablity attenuate pathophysiological responses. The ability to screen for antagonists and/or agonists which modulate the biological and/or pharmacological activity of the native human tyrosine kinase molecule as described herein is significantly valuable toward the identification and development of therapeutic agents. Moreover, diagnostic applications are readily apparent for the detection of pathophysiological conditions manifested by abnormal levels of molecules such as SEQ ID NO:2 and/or SEQ ID NO:3 by means of PCR sequence amplification and subsequent detection and/or antibody based assays, e.g., ELISA-based assays, which are well-known to those skilled in the art and readily performed provided the information disclosed herein.

The present invention relates to nucleic acid sequences and amino acid sequences of the tyrosine kinase and variants thereof and to the use of these sequences to identify compounds that modulate the biological and/or pharmacological activity of a signal transduction molecule.

Polynucleotide sequences which encode the tyrosine kinase as depicted in SEQ ID NO:3 and variants thereof contemplated herein are particularly preferred embodiment of the present invention. Biologically effective antisense molecules and nucleic acids which encode biologically effective dominant negative mutant versions of SEQ ID NO:3, or derivatives thereof, as well as dominant negative mutant versions of SEQ ID NO:3, and derivatives thereof, examples of each of which are described infra, are preferred embodiments of the present invention and are intended to fall within the scope of the claims appended hereto.

The present invention also provides a method of treatment for a patient in need of such treatment, videlicet for a patient who suffers a pathological condition mediated by the SEQ ID NO:3 tyrosine kinase or another signal transduction molecule or a downstream transcriptional activator, comprising administering an effective amount of a biologically effective antisense nucleic acid molecule derived from SEQ ID NO:1 or SEQ ID NO:2; or administering an effective amount of a nucleic acid which encodes a biologically effective dominant negative mutant version of the tyrosine kinase; or administering a compound that modulates the biological and/or pharmacological activity of SEQ ID NO:3 which was identified by a method described herein.

The present invention relates to nucleic acid sequences (e.g., SEQ ID NO: 1 and SEQ ID NO:2) and amino acid sequences (e.g., SEQ ID NO:3; SEQ ID NO:3 positions 1–25, SEQ ID NO:3 positions 1–122, SEQ ID NO:3 positions 26–422, and SEQ ID NO:3 positions 123–422) of the novel human signal transduction kinase as well as inherent derivatives thereof, e.g., functional derivative that demonstrate or perform substantially the same biological and/or pharmacological activity in substantially the same way. The invention is also intended to encompass biologically and/or pharmacologically active truncated versions clearly derived from the sequences disclosed and characterized herein (e.g., evidenced domains described infra) as well as chimeric sequences which contain one or more of them.

Variants

The present invention relates to variants of nucleic acid sequences sequences (e.g., SEQ ID NO:1 and SEQ ID NO:2) and amino acid sequences (e.g., SEQ ID NO:3) substantially as shown, which have changes, e.g., a polypeptide sequence comprising a sequence which differs from the sequence referred to by at least one amino acid substitution, preferrably a conservative amino acid substitution, that demonstrate or perform substantially the same biological and/or pharmacological activity in substantially the same way, as well as molecules which comprise truncated versions of these variants. However, variant as used herein is intended to encompass all contemplated biologically effective dominant negative mutants, several species of which are set forth herein.

A preferred variant, as depicted in SEQ ID NO:3 for instance, is one having at least 80% amino acid sequence homology (identity) to SEQ ID NO:3; a more preferred variant is one having at least 90% amino acid sequence homology; and a most preferred variant is one having at least 95% amino acid sequence homology to the kinase molecule amino acid sequence as depicted in SEQ ID NO:3 or a biologically and/or pharmacologically active substantial fragment thereof. Variants within the scope of this invention also include biologically-effective dominant negative mutants of these contemplated embodiments.

A variant of the SEQ ID NO:3 human kinase molecule of the present invention may have an amino acid sequence that is different by one or more amino acid substitutions. Embodiments which comprise amino acid deletions and/or additions are also contemplated. The variant may have conservative changes (amino acid similarity), wherein a substituted amino acid has similar structural or chemical properties, for example, the replacement of leucine with isoleucine. A variant may have nonconservative changes, e.g., replacement of a glycine with a tryptophan. Embodiments within the intended scope of the invention also include SEQ ID NO:3 having one or more amino acid deletions or insertions, or both. Guidance in determining which and how many amino acid residues may be substituted, inserted or deleted without abolishing biological or proposed pharmacological activity may be reasonably inferred in view of this disclosure and may be further be found using computer programs well known in the art, for example, DNAStar software.

Amino acid substitutions of SEQ ID NO:3 may be made, for instance, on the basis of similarity in polarity, charge, solubility, hydrophobicity, hydrophilicity, and/or the amphipathic nature of the residues as long as a biological and/or pharmacological activity of the native molecule is retained. However, amino acid substitutions are important to construct contemplated biologically effective dominant negative mutants, several species of which are set forth herein.

Negatively charged amino acids, for example, include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine. However, in the construction of biologically effective dominant negative mutants at least one amino acid residue position at an active site required for biological and/or pharmacological activity in the native peptide is changed to produce an agent or entity having reduced activity or which is devoid of detectable native wild type activity.

Suitable substitutions of amino acids include the use of a chemically derivatized residue in place of a non-derivatized residue. D-isomers as well as other known derivatives may also be substituted for the naturally occurring amino acids. See, e.g., U.S. Pat. No. 5,652,369, Amino Acid Derivatives, issued Jul. 29, 1997. Example substitutions are set forth in TABLE 1 as follows:

TABLE 1

| Original residue | Example conservative substitutions |
| --- | --- |
| Ala (A) | Gly; Ser; Val; Leu; Ile; Pro |
| Arg (R) | Lys; His; Gln; Asn |
| Asn (N) | Gln; His; Lys; Arg |
| Asp (D) | Glu |
| Cys (C) | Ser |
| Gln (Q) | Asn |
| Glu (E) | Asp |
| Gly (G) | Ala; Pro |
| His (H) | Asn; Gln; Arg; Lys |
| Ile (I) | Leu; Val; Met; Ala; Phe |
| Leu (L) | Ile; Val; Met; Ala; Phe |
| Lys (K) | Arg; Gln; His; Asn |
| Met (M) | Leu; Tyr; Ile; Phe |
| Phe (F) | Met; Leu; Tyr; Val; Ile; Ala |
| Pro (P) | Ala; Gly |
| Ser (S) | Thr |
| Thr (T) | Ser |
| Trp (W) | Tyr; Phe |
| Tyr (Y) | Trp; Phe; Thr; Ser |
| Val (V) | Ile; Leu; Met; Phe; Ala |

"Homology" is a measure of the identity of nucleotide sequences or amino acid sequences. In order to characterize the homology, subject sequences are aligned so that the highest order homology (match) is obtained. "Identity" per se has an art-recognized meaning and can be calculated using published techniques. Computer program methods to determine identity between two sequences, for example, include DNAStar software (DNAStar Inc., Madison, Wis.);

the GCG program package (Devereux, J., et al., Nucleic Acids Research (1984) 12(1):387); BLASTP, BLASTN, FASTA (Atschul, S. F. et al., J Molec Biol (1990) 215:403). Homology (identity) as defined herein is determined conventionally using the well known computer program, BESTFIT (Wisconsin Sequence Analysis Package, Version 8 for Unix, Genetics Computer Group, University Research Park, 575 Science Drive, Madison, Wis. 53711). When using BESTFIT or any other sequence alignment program to determine whether a particular sequence is, for example, about 80% homologous to a reference sequence, according to the present invention, the parameters are set such that the percentage of identity is calculated over the full length of the reference nucleotide sequence or amino acid sequence and that gaps in homology of up to about 20% of the total number of nucleotides in the reference sequence are allowed. Eighty percent of homology is therefore determined, for example, using the BESTFIT program with parameters set such that the percentage of identity is calculated over the full length of the reference sequence, e.g., SEQ ID NO:3, and gaps of up to 20% of the total number of amino acids in the reference sequence are allowed, and wherein up to 20% of the amino acid residues in the reference sequence may be deleted or substituted with another amino acid, or a number of amino acids up to 20% of the total amino acid residues in the reference sequence may be inserted into the reference sequence. Percent homologies are likewise determined, for example, to identify preferred species, within the scope of the claims appended hereto, which reside within the range of about 80 percent to 100 percent homology to SEQ ID NO:3 as well as biologically and/or pharmacologically active functional derivatives thereof and biologically effective dominant negative mutants contemplated herein.

Percentage similarity (conservative substitutions) between two polypeptides may also be scored by comparing the amino acid sequences of the two polypeptides by using programs well known in the art, including the BESTFIT program, by employing default settings for determining similarity.

The present invention relates, in part, to the inclusion of the polynucleotide encoding the tyrosine kinase molecule in an expression vector which can be used to transform host cells or organisms. Such transgenic hosts are useful for the production of the protein kinase as well as valuable variations thereof contemplated herein.

The nucleic acid sequence also provides for the design of antisense molecules, example embodiments of which are provided herein, which are useful in downregulating, diminishing, or eliminating expression, e.g., transcription and/or translation of SEQ ID NO:2 in cells.

The receptor tyrosine kinase molecule of the present invention is used in screening assays to identify antagonists or inhibitors which bind the kinase, emulate its substrate, or otherwise inactivate the biomolecule or compete biologically, e.g., competitive interaction or competitive binding inhibition, with the native SEQ ID NO:3 biomolecule. The tyrosine kinase can also be used in screening assays to identify agonists which agonize or mimic the biological and/or pharmacological activity, induce the production of or prolong the biological halflife of the molecule in vivo or in vitro.

The invention also relates to pharmaceutical compositions which comprise molecules as depicted in SEQ ID NO:2 or SEQ ID NO:3 or variants of these molecules as defined herein for the treatment of pathological disorders related to or mediated by the tyrosine kinase of the present invention.

Example Embodiments and Dominant Negative Mutants

A purified polynucleotide is preferred which comprises a nucleic acid sequence which encodes a polypeptide comprising the sequence as depicted in SEQ ID NO:3 or a variant of SEQ ID NO:3, including but not limited to SEQ ID NO:3 wherein position 147 (Lysine) of SEQ ID NO:3 is substituted or deleted, SEQ ID NO:3 positions 1–25 (extracellular domain for interaction with other molecules including ligands or agonist/antagonists), SEQ ID NO:3 positions 1–122 (non-kinase domain which can be used as a dominant negative form), SEQ ID NO:3 positions 26–422 (intracellular functional domain which also can be used to make chimera with other known extracellular proteins), and SEQ ID NO:3 positions 123–422 (tyrosine kinase domain which can be used for screening compounds (as well as in assay protocols)).

The tyrosine kinase (SEQ ID NO:3) coding region, SEQ ID NO:2, can be obtained from existing cDNA, for example, by PCR amplication using primers derived from SEQ ID NO: 1. See, e.g., Example I. SEQ ID NO:2, for example, (as well as variations thereof) may be inserted into expression vectors, with or without fusion protein "tags", for expression of a protein, e.g., SEQ ID NO:3, which can be purified and screened for biological and/or pharmacological activity, including signal transduction activity, and substrate activation. Prokaryotic expression vectors may be used including the likes of, for example, pGEX (GST fusion), pET (+/−His$_6$ or T7 tag), as well as eukaryotic expression vectors including the likes of, for example, pcDNA3.1His, pIRES-EGFP, pcDNA3, and pEBVHis. Recombinant proteins, derived from SEQ ID NO:3, are provided for use in screening assays for the identification of compounds which may modulate the biological and/or pharmacological activity of tyrosine kinases.

An example dominant negative mutant of SEQ ID NO:3 (lysine at position 147 changed to arginine) is set forth as an embodiment predicted to be catalytically inactive.

Antisense Molecules

Various nucleic acid sequences complementary to SEQ ID NO:1 and/or SEQ ID NO:2 provided herein may be used in another embodiment of the invention to modulate the expression of a tyrosine kinase or biological function of a downstream signal transduction molecule or transcriptional activator, including but not limited to Cdc2 kinase, by affecting the transcription and/or translation of sequences corresponding to the novel tyrosine kinase (SEQ ID NO:1 and/or SEQ ID NO:2) in cells. Pharmacological activity of the endogenous gene may be modulated by affecting the transcription and/or translation, for example, of the endogenous gene by use or administration of anti-sense constructs to produce anti-sense transcripts or by direct delivery of anti-sense oligomers. Antisense constructs and oligomers may each be used as embodiments of the present invention and each are related to therapeutic method embodiments practiced via direct administration as defined herein. Translation is most effectively inhibited by blocking the mRNA at a site at or near the initiation or termination codon. Thus, oligonucleotides complementary to the 5' or 3'-terminal region of the receptor tyrosine kinase mRNA transcript are preferred. Example species are provided.

Antisense molecules which comprise oligomers in the range from about 12 to about 25 nucleotides which are complementary the regions of SEQ ID NO:1 and/or 5' region pSEQ ID NO:2 which are proximal to, or include, the translational start or stop codon, or a portion thereof, are preferred embodiments of the invention. Antisense molecules comprising oligomers from about 12 to about 25 nucleotides in length which are complementary to a region within the SEQ ID NO:1 positions 67–148 or 1333–1414 are particularly preferred embodiments. Oligonucleotides which comprise sequences complementary to the following positions of SEQ ID NO: 1 are example embodiments of the invention:

SEQ ID NO:1 positions 67–79; 70–82; 73–85; 75–92; 76–88; 79–91; 80–92; 81–93; 82–94; 83–95; 84–96; 85–97; 86–98; 87–99; 88–100; 89–101; 90–102; 91–103; 92–104; 93–105; 94–106; 95–107; 96–108; 97–109; 98–110; 99–111; 100–112; 101–113; 102–114; 103–115; 104–116; 105–117; 106–118; 107–119; 108–120; 109–121; 110–122; 111–123; 112–124; 113–125; 114–126; 115–127; 116–128; 117–129; 118–130; 119–131; 120–132; 121–133; 122–134; 123–135; 124–136; 125–137; 126–138; 127–139; 128–140; and 136–148.

SEQ ID NO:1 positions 1333–1345; 1336–1348; 1339–1351; 1342–1354; 1345–1357; 1346–1358; 1347–1359; 1348–1360; 1348–1365; 1349–1361; 1350–1362; 1351–1363; 1352–1364; 1353–1365; 1354–1366; 1355–1367; 1356–1368; 1357–1369; 1358–1370; 1359–1371; 1360–1372; 1361–1373; 1362–1374; 1363–1375; 1364–1376; 1365–1377; 1366–1378; 1367–1379; 1368–1380; 1369–1381; 1370–1382; 1371–1383; 1372–1384; 1373–1385; 1374–1386; 1375–1387; 1376–1388; 1377–1389; 1378–1390; 1379–1391; 1380–1392; 1381–1393; 1382–1394; 1383–1395; 1384–1396; 1385–1397; 1386–1398; 1387–1399; 1388–1400; 1389–1401; 1390–1402; 1391–1403; 1392–1404; 1393–1405; 1394–1406; and 1412–1414.

Oligonucleotides which comprise sequences complementary to and hybridizable to each of the recited areas of the human receptor tyrosine kinase mRNA are contemplated for therapeutic use. Moreover, U.S. Pat. No. 5,639,595, Identification of Novel Drugs and Reagents, issued Jun. 17, 1997, wherein methods of identifying oligonucleotide sequences that display in vivo activity are thoroughly described, is herein incorporated by reference.

Nucleotide sequences that are complementary to the tyrosine kinase encoding nucleic acid sequence can be synthesized for antisense therapy. These antisense molecules may be DNA, stable derivatives of DNA such as phosphorothioates or methylphosphonates, RNA, stable derivatives of RNA such as 2'-O-alkylRNA, or other oligonucleotide mimetics. U.S. Pat. No. 5,652,355, Hybrid Oligonucleotide Phosphorothioates, issued Jul. 29, 1997, and U.S. Pat. No. 5,652,356, Inverted Chimeric and Hybrid Oligonucleotides, issued Jul. 29, 1997, which describe the synthesis and effect of physiologically-stable antisense molecules, are incorporated by reference. Tyrosine kinase antisense molecules may be introduced into cells by microinjection, liposome encapsulation or by expression from vectors harboring the antisense sequence. Antisense therapy may be particularly useful for the treatment of diseases where it is beneficial to modulate the effective biological and/or pharmacological activity of the tyrosine kinase presented herein.

Gene Therapy

Embodiments of tyrosine kinase nucleic acids or dominant negative mutant versions thereof as well as antisense embodiments described herein may be administered to a subject via gene therapy to modulate, i.e., boost or attenuate the corresponding biological and/or pharmacological activity or gene expression of an endogenous tyrosine kinase. Nucleic acid sequences of the present invention may be delivered ex vivo or in vivo to the cells of target organs in a tissue-specific manner. The human tyrosine kinase polypeptide coding region can be ligated into viral vectors which mediate transfer of the kinase polypeptide DNA by infection of recipient host cells. Suitable viral vectors include retrovirus, adenovirus, adeno-associated virus, herpes virus, vaccinia virus, polio virus and the like. See, e.g., U.S. Pat. No. 5,624,820, Episomal Expression Vector for Human Gene Therapy, issued Apr. 29, 1997. GENOVO Corporation, for instance, Sharon Hill, Pa., at the date of this application, have a readily commercially available expression vector portfolio which comprise an assortment of vectors complete with well-established methods which consistently demonstrate tissue-specific expression. The GENOVO Corporation is an example source for vectors and methods to practice gene-therapy methods of the present invention. Nucleic acid coding regions of the present invention are incorporated into effective expression vectors, which are directly administered or introduced into somatic cells for gene therapy (a nucleic acid fragment comprising a coding region, preferably mRNA transcripts, may also be administered directly or introduced into somatic cells). See, e.g., U.S. Pat. No. 5,589,466, issued Dec. 31, 1996. Such nucleic acids and vectors may remain episomal or may be incorporated into the host chromosomal DNA as a provirus or portion thereof that includes the gene fusion and appropriate eukaryotic transcription and translation signals, i.e, an effectively positioned RNA polymerase promoter 5' to the transcriptional start site and ATG translation initiation codon of the gene fusion as well as termination codon(s) and transcript polyadenylation signals effectively positioned 3' to the coding region. Alternatively, the human tyrosine kinase polypeptide DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection. These procedures and variations thereof are suitable for ex vivo, as well as in vivo human tyrosine kinase polypeptide gene therapy according to established methods in this art.

Generally Acceptable Vectors

In accordance with the present invention, polynucleotide sequences which encode the tyrosine kinase, fragments of the polypeptide, fusion proteins or functional equivalents thereof may be used in recombinant DNA molecules that direct the expression of the respective molecule in appropriate host cells. Due to the inherent degeneracy of the genetic code, other DNA sequences which encode substantially the same or a functionally equivalent amino acid sequence may be used to clone and express the tyrosine kinase, as well as variations thereto and dominant negative mutants thereof. As will be understood by those of skill in the art, it may be advantageous to produce nucleotide sequences possessing non-naturally occurring codons.

Cloned tyrosine kinase cDNA obtained through the methods described herein may be recombinantly expressed by molecular cloning into an expression vector containing a suitable promoter and other appropriate transcription regulatory elements, and transferred into prokaryotic or eukaryotic host cells to produce the receptor kinase. Techniques for such manipulations are fully described in Sambrook, J., et al., Molecular Cloning Second Edition, Cold Spring Harbor Press (1990), and are well known in the art.

Expression vectors are described herein as nucleic acid sequences for the transcription of embodiments of the present invention. Such vectors can be used to express nucleic acid sequences in a variety of hosts such as bacteria, bluegreen algae, plant cells, insect cells, fungal cells, human, and animal cells. Specifically designed vectors allow the shuttling of DNA between hosts such as bacteria-yeast, or bacteria-animal cells, or bacteria-fungal cells, or bacteria-invertebrate cells.

A variety of mammalian expression vectors may be used to express the recombinant human tyrosine kinase molecule as well as variants contemplated herein. Commercially available mammalian expression vectors which are suitable for recombinant expression, include but are not limited to, pcDNA3 (Invitrogen), pMClneo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and IZD35 (ATCC 37565), pLXIN and pSIR (CLONTECH), pIRES-EGFP (CLONTECH). INVITROGEN corporation provides a wide variety of commercially available mammalian expression vector/systems which can be effectively used with the present invention. INVITROGEN, Carlsbad, Calif. See, also, PHARMINGEN products, vectors and systems, San Diego, Calif.

Baculoviral expression systems may also be used with the present invention to produce high yields of biologically active kinase. Vectors such as the CLONETECH, BacPak™ Baculovirus expression system and protocols are preferred which are commercially available. CLONTECH, Palo Alto, Calif. Miller, L. K., et al., Curr. Op. Genet. Dev. 3:97 (1993); O'Reilly, D. R., et al., *Baculovirus Expression Vectors: A Laboratory Manual*, 127. Vectors such as the INVITROGEN, MaxBac™ Baculovirus expression system, insect cells, and protocols are also preferred which are commercially available. INVITROGEN, Carlsbad, Calif.

Example Host Cells

Host cells transformed with a nucleotide sequence which encodes the signal transduction molecule of the present invention may be cultured under conditions suitable for the expression and recovery of the encoded protein from cell culture. Particularly preferred embodiments of the present invention are host cells transformed with a purified polynucleotide comprising a nucleic acid sequence to encode the polypeptide having the sequence as depicted in SEQ ID NO:3 or a contemplated variant thereof. Cells of this type or preparations made from them may be used to screen for modulators of the biological and/or pharmacological activity of the native tyrosine kinase signal transduction molecules SEQ ID NO:1, SEQ ID NO:2, and SEQ ID NO:3.

Eukaryotic recombinant host cells are especially preferred. Examples include but are not limited to yeast, mammalian cells including but not limited to cell lines of human, bovine, porcine, monkey and rodent origin, and insect cells including but not limited to Drosophila and silkworm derived cell lines. Cell lines derived from mammalian species which may be suitable and which are commercially available, include but are not limited to, L cells L-M(TK-) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/1/3T3 (ATCC CRL 1658), HeLa (ATCC CCL 2), C127I (ATCC CRL 1616),BS-C-1 (ATCC CCL 26) and MRC-5 (ATCC CCL 171).

The expression vector may be introduced into host cells expressing the novel tyrosine kinase via any one of a number of techniques including but not limited to transformation, transfection, lipofection, protoplast fusion, and electroporation. Commercially available kits applicable for use with the present invention for hererologous expression, including well-characterized vectors, transfection reagents and conditions, and cell culture materials are well-established and readily available. CLONTECH, Palo Alto, Calif.; INVITROGEN, Carlsbad, Calif.; PHARMINGEN, San Diego, Calif.; STRATAGENE, LaJolla, Calif. The expression vector-containing cells are clonally propagated and individually analyzed to determine the level of tyrosine kinase poypeptide production. Identification of host cell clones which express the novel kinase may be performed by several means, including but not limited to immunological reactivity with antibodies described herein, and/or the presence of host cell-associated specific biological activity, and/or the ability to covalently cross-link specific substrate to the receptor tyrosine kinase with the bifunctional cross-linking reagent disuccinimidyl suberate or similar cross-linking reagents.

The signal transduction molecule of the present invention may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals (Porath, J., Protein Exp. Purif. 3:263 (1992)), protein A domains that allow purification on immobilized immunoglobulin, and the domain utilized in the FLAGS extension/affinity purification system (Immunex Corp, Seattle Wash.). The inclusion of a cleavable linker sequences such as Factor XA or enterokinase (Invitrogen, San Diego Calif.) between the purification domain and the coding region is useful to facilitate purification.

Systems such as the CLONTECH, TALON™ nondenaturing protein purification kit for purifying 6xHis-tagged proteins under native conditions and protocols are preferred which are commercially available. CLONTECH, Palo Alto, Calif.

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a nascent form of the protein may also be important for correct insertion, folding and/or function. Different host cells such as CHO, HeLa, MDCK, 293, WI38, NIH-3T3, HEK293 etc., have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express SEQ ID NO:2/SEQ ID NO:3, for example, may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

The signal transduction molecule, e.g., SEQ ID NO:3, can be produced in the yeast *S.cerevisiae* following the insertion of the optimal cDNA cistron into expression vectors designed to direct the intracellular or extracellular expression of the heterologous protein. In the case of intracellular expression, vectors such as EmBLyex4 or the like are ligated to the beta subunit cistron. See, e.g., Rinas, U., et al., Biotechnology, 8:543 (1990); Horowitz, B., et al., J. Biol. Chem., 265:4189 (1989). For extracellular expression, the kinase cistron is ligated into yeast expression vectors which may employ any of a series of well-characterized secretion signals. The levels of expressed novel kinase are determined by the assays described herein.

A variety of protocols for detecting and measuring the expression of the novel molecule as well as functional derivatives thereof, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes may be employed. Well known competitive binding techniques may also be employed. See, e.g., Hampton, R., et al. (1990), *Serological Methods—a Laboratory Manual*, APS Press, St Paul Minn.; Maddox, D. E., et al., J. Exp. Med. 158:1211.

Screening Assays

Methods are provided to screen compounds individually or by the employment of libraries of compounds for the identification of compounds which have the ability to modulate a biological and/or pharmacological activity of a receptor tyrosine kinase, e.g., SEQ ID NO:3 described herein. The present invention is also directed to methods of screening for compounds which modulate the expression (transcription and/or translation) of DNA or RNA encoding the tyrosine kinase polypeptide SEQ ID NO:3. Compounds which modulate these activities may be DNA, RNA, peptides, proteins, or non-proteinaceous organic molecules (e.g., small molecule drug compounds).

Compounds may modulate an ultimate biological and/or pharmacological activity by increasing or attenuating the expression of DNA or RNA encoding the human signal-transduction biomolecule or a function of the native SEQ ID NO:3. Compounds that modulate the expression of DNA or RNA encoding the tyrosine kinase polypeptide or the function of the polypeptide may be detected by a variety of assays. The assay may be a simple "yes/no" assay to determine whether there is a change in expression or function. The assay may be made quantitative by comparing the expression or function of a test sample with the levels of expression or function in a standard sample.

The human receptor tyrosine kinase described herein, SEQ ID NO:3, its functional fragments or oligopeptides including but not limited to SEQ ID NO:3 positions 1–25, SEQ ID NO:3 positions 1–122, SEQ ID NO:3 positions 26–422, and SEQ ID NO:3 positions 123–422, as well as variants contemplated herein can be used for screening prospective therapeutic compounds in any of a variety of drug screening techniques. The fragment or entity employed in such a test may be free in solution, affixed to a solid support, borne on a cell surface, or located intracellularly. The abolition or modulation of activity or the formation of binding complexes, between the human signal-transduction kinase and the agent being tested, may be measured, for example, by means provided.

It is expected that the novel human signal transduction receptor tyrosine kinase will have high catalytic activity that will permit easy adaptation to automated high throughput screening assays, including scintillation proximity assays, which are well known in the art. See, e.g., U.S. Pat. No. 5,763,198, Screening Assays for Compounds, issued Jun. 9, 1998 (an example rapid, quantitative, specific, high through-put assay systems for screening test compounds such as drugs, ligands (natural or synthetic), ligand antagonists, peptides, or small organic molecules for their ability to modulate tyrosine kinase activity within the cell or in a cell-free system); U.S. Pat. No. 5,763,584, Receptor Activation with Hepatocyte Growth Factor Agonists, issued Jun. 9, 1998 (an example method for activating receptors selected from receptor tyrosine kinases and for making ligand variants that act as competitive agonists of the respective native ligands); and, U.S. Pat. No. 5,763,441, Compounds for the Treatment of Disorders Related to Vasculogenesis and/or Angiogenesis, issued Jun. 9, 1998, which are herein incorporated by reference as examples. Moreover, Scintillation Proximity Assay (SPA) technology is set forth as an embodiment which allows rapid and sensitive assay of a wide variety of molecular interactions in a homogeneous system (AMERSHAM, Bucks, UK).

Accordingly, the present invention provides a method for screening a plurality of compounds for specific binding affinity with the native polypeptide SEQ ID NO:3 or a variant thereof contemplated herein, comprising providing a plurality of compounds; combining an embodiment of the tyrosine kinase of the present invention with each of a plurality of compounds for a time sufficient to allow binding under suitable conditions; and detecting binding of the kinase polypeptide, or fragment thereof, to each of the plurality of compounds, thereby identifying the compounds which specifically bind the signal-transduction kinase polypeptide.

Methods of identifying compounds that modulate a biological and/or pharmacological activity of a signal transduction molecule are generally preferred, which comprise combining a candidate compound modulator of signal transduction activity (biological and/or pharmancological) with a polypeptide having the sequence as depicted in SEQ ID NO:3 or a variant thereof contemplated herein, and measuring an effect of the candidate compound modulator on the biological and/or pharmacological activity of the polypeptide. The kinase activity of the biomolecule may be assayed and/or to the performance of any one or more of the functions including but not limited to the ability to autophosphorylate, to phosphorylate a substrate, to bind ATP, and to mediate the activation of Cdc2 kinase. The pharmacological activity of the biomolecule may be assayed by means of comparing, to control cells, for example, the manifestation and rate of mitosis, cell differentiation, proliferation, oncogenic transformation, neoplasia, cell aggregation, and cytokinesis.

Assays for the novel receptor tyrosine kinase, kinase activity, are performed via well known ser/thr kinase assays, except MBP is substituted with enolase. Cooper, et al., J. Biol. Chem., 259:7835 (1984). Phosphorylation sites in enolase are utilized by tyrosine protein kinases in vivo and in vitro. See, Examples V and VI.

The ability of the receptor tyrosine kinase to phosphorylate a substrate and/or bind a cognate ligand may be measured by methods well-known to those skilled in the art. See, e.g., U.S. Pat. No. 5,763,584, Receptor Activation with Hepatocyte Growth Factor Agonists, issued Jun. 9, 1998 (an example method for activating receptors selected from receptor tyrosine kinases and for making ligand variants that act as competitive agonists of the respective native ligands); U.S. Pat. No. 5,763,198, Screening Assays for Compounds, issued Jun. 9, 1998 (an example rapid, quantitative, specific, high through-put assay systems for screening test compounds such as drugs, ligands (natural or synthetic), ligand antagonists, peptides, or small organic molecules for their ability to modulate tyrosine kinase activity within the cell or in a cell-free system); and, U.S. Pat. No. 5,763,441, Compounds for the Treatment of Disorders Related to Vasculogenesis and/or Angiogenesis, issued Jun. 9, 1998, which are herein incorporated by reference as examples.

Biological activity as used herein in reference to the tyrosine kinase of the present invention refers to inter alia mediation of activation of Cdc2 kinase which mediates mitosis. See, e.g., Nishio K., et al., Antitumor effects of butyrolactone I, a selective cdc2 kinase inhibitor, on human lung cancer cell lines, Anticancer Research, 16(6B):3387 (1996); Vincent I., et al., Aberrant expression of mitotic cdc2/cyclin B1 kinase in degenerating neurons of Alzheimer's disease brain, Journal of Neuroscience, 17(10):3588 (1997).

Accordingly, methods of identifying compounds that modulate a biological and/or pharmacological activity of a tyrosine kinase are particularly preferred which comprise combining a candidate compound modulator with a host-cell expressing a polypeptide having the sequence as depicted in SEQ ID NO:3 or a variant thereof contemplated herein and measuring an effect of the candidate compound modulator on the biological and/or pharmacological activity of the polypeptide. Preferred cellular assays for modulators of the subject tyrosine kinase signal transduction molecule fall into two general categories: 1) direct measurement of a biological activity, and 2) measurement of downstream events in the signaling cascade including cell/tissue/organism physiological manifestations.

In order to measure activity of the tyrosine kinase, the source of the molecule to be assayed may be a whole cell lysate, prepared by one to three freeze-thaw cycles in the presence of standard protease inhibitors. Alternatively, the kinase may be partially or completely purified by standard protein purification methods. The kinase may be purified by affinity chromatography using antibodies described herein or by ligands specific for the epitope tag engineered into the recombinant kinase moreover described herein. The preparation may then be assayed for activity. Example assays used to screen for compounds which modulate kinase activity, for example, are set forth infra. See, e.g., Examples V and VI.

In another method embodiment of the invention to identify agents which modulate a biological activity of the novel biomolecule set forth herein, a nucleic acid sequence which encodes a signal-transduction molecule, for example as depicted in SEQ ID NO:3, may be ligated to a heterologous sequence to encode a fusion protein for use in a yeast 2-hybrid system. To screen compounds for the modulation of SEQ ID NO:3 biological activity, it is necessary to encode a chimeric peptide for expression in hererologous host cells. Chimeric constructs are also used to express a 'bait', according to methods well known using a yeast two-hybrid system, using accessory native peptides that are expected to be associated with the tyrosine kinase molecule described herein. The two-hybrid system uses the ability of a pair of interacting proteins to bring a transcription activation domain into close proximity with a DNA-binding site that regulates the expression of an adjacent reporter gene. Compounds which are able to modulate the biological activity of the novel biomolecule as defined herein are identified by the their ability to effect protein:protein interactions (reconstitution of the chimeric transcriptional activators) and hence the yeast 2-hybrid readout assays well-known to artisans of ordinary skill in this area of molecular biology. Fields, S., et al., Trends Genet., 10:286 (1994); Allen, J. B., et al., TIBS, 20:511 (1995). Fields, S., Song, O., Nature 340:245 (1989). Commercially available systems such as the CLONTECH, Matchmaker™ systems and protocols may be used with the present invention. CLONTECH, Palo Alto, Calif. See also, Mendelsohn, A. R., Brent, R., Curr. Op. Biotech., 5:482 (1994); Phizicky. E. M., Fields, S., Microbiological Rev., 59(1):94 (1995); Yang, M., et al., Nucleic Acids Res., 23(7):1152 (1995); Fields, S., Sternglanz, R., TIG, 10(8):286 (1994); and U.S. Pat. No. 5,283,173, System to Detect Protein-Protein Interactions, and U.S. Pat. No. 5,468,614, which are incorporated herein by reference.

To further evaluate the ability of a compound to modulate the pharmacological activity, for example, of SEQ ID NO:3, human tumor cells are injected into SCID mice (severe combined immunodeficiency) to form palpable tumor masses. See, Example VII.

Compounds which are identified generally according to methods described, contemplated, and referenced herein that modulate a biological and/or pharmacological activity of a human receptor tyrosine kinase of the sequence as depicted in SEQ ID NO:3 are especially preferred embodiments of the present invention.

An especially preferred embodiment of the present invention is a method for treatment of a patient in need of such treatment for a condition which is mediated by the tyrosine kinase molecule described herein, e.g., SEQ ID NO:3, comprising administration of a therapeutically effective amount of a modulating compound identified using sequences as depicted in SEQ ID NO:1, SEQ ID NO:2 and/or SEQ ID NO:3 or a contemplated variant thereof as a pharmacological target in methods contemplated herein.

A method of modulating a biological and/or pharmacological activity of a signal transduction kinase in a cell, tissue, or organism is preferred which comprises administering an effective amount of a polynucleotide contemplated herein. 'Polynucleotide' includes a polynucleotide comprising a nucleic acid sequence which encodes a polypeptide having at least about 80% homology to SEQ ID NO:3, SEQ ID NO:3 positions 1–25, SEQ ID NO:3 positions 1–122, SEQ ID NO:3 positions 26–422, and SEQ ID NO:3 positions 123–422; as well as a polynucleotide comprising a nucleic acid sequence which encodes a polypeptide comprising the sequence as depicted in SEQ ID NO:3 wherein position 147 (Lysine) of SEQ ID NO:3 is substituted or deleted; as well as antisense molecules which are complementary to a region within SEQ ID NO:1 positions 67–148 or 1333–1414, example therapeutic embodiments of which are set forth supra.

Antibodies

The receptor tyrosine kinase can be used to raise diagnostic antibodies as to detect abnormal levels of the biomoleule in vivo. Therefore, in accordance with yet a further aspect of the present invention, there are provided antibodies against the receptor tyrosine kinase poypeptide which may used as part of various diagnostic assays for detecting physiological disorders including cancer tissue. An example for the production of effective polyclonal antibodies against peptides derived from SEQ ID NO:3, for employment in methods described herein, is EADRPSPRELRLRLE (SEQ ID NO:4) which was identified within the c-terminal region of the novel human tyrosine kinase (SEQ ID NO:3) utilizing a well established algorithm method developed by Jameson and Wolf. *The antigenic Index: A novel Algorithm for Predicting Antigenic Determinants*, CABIOS, 4:181 (1988). This peptide was conjugated to keyhole limpet hemocyanin and used for antibody generation by GENOSYS BIOTECHNOLOGIES, 1442 Lake Front Circle, Suite 185, The Woodlands, Tex. 77380. Specific antibodies may be raised by immunizing animals, with rabbits being preferred, with an appropriate concentration of the human tyrosine kinase either with or without an immune adjuvant.

Monospecific antibodies to the polypeptide of the present invention are purified from mammalian antisera containing antibodies reactive against the polypeptide or are prepared as monoclonal antibodies reactive with the signal transduction polypeptide using the technique of Kohler and Milstein, Nature, 256:495 (1975). Mono-specific antibody as used herein is defined as a single antibody species or multiple antibody species with homogenous binding characteristics for the novel signal transduction molecule. Homogenous binding as used herein refers to the ability of the antibody species to bind to a specific antigen or epitope, such as those associated with SEQ ID NO:3. Monoclonal antibodies are produced in vivo by injection of pristane primed Balb/c mice, approximately 0.5 ml per mouse, with about $2\times10^6$ to about $6\times10^6$ hybridoma cells about 4 days after priming. Ascites fluid is collected at approximately 8–12 days after cell transfer and the monoclonal antibodies are purified by techniques known in the art. In vitro production of the anti-polypeptide mAb is carried out by growing the hydridoma in DMEM containing about 2% fetal calf serum to obtain sufficient quantities of the specific mAb. The mAb are purified by techniques known in the art.

Purification of SEQ ID NO:3 via Affinity Columns

It is readily apparent to those skilled in the art that methods for producing antibodies may be utilized to produce antibodies specific for the tyrosine kinase polypeptide fragments, or the full-length nascent polypeptide, e.g., SEQ ID NO:3. Specifically, it is readily apparent to those skilled in the art that antibodies may be generated which are specific for the fully functional protein and fragments and variants thereof.

Tyrosine kinase polypeptide antibody affinity columns are made by adding the antibodies to Affigel-10 (Biorad), a gel support which is activated with N hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) with appropriate detergent and the cell culture supernatants or cell extracts containing human tyrosine kinase polypeptide made using appropriate membrane solubilizing detergents are slowly passed through the column. The column is then washed with phosphate buffered saline/detergent until the optical density falls to background, then the protein is eluted with 0.23M glycine-HCl (pH 2.6)/detergent. The purified polypeptide is then dialyzed against phosphate buffered saline/detergent.

Recombinant tyrosine kinase molecules can be separated from other cellular proteins by use of an immunoaffinity column made with monoclonal or polyclonal antibodies specific for full length nascent signal transduction polypeptide, or polypeptide fragments.

Polypeptides described herein may be used to affinity purify biological effectors from native biological materials, e.g. disease tissue. Affinity chromatography techniques are well known to those skilled in the art. A tyrosine kinase peptide described herein or an effective fragment thereof, is fixed to a solid matrix, e.g. CNBr activated Sepharose according to the protocol of the supplier (Pharmacia, Piscataway, N.J.), and a homogenized/buffered cellular solution containing a potential molecule of interest is passed through the column. After washing, the column retains only the biological effector which is subsequently eluted, e.g., using 0.5M acetic acid or a NaCl gradient.

Diagnostic Assays

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar diagnostic assays are used to detect the presence of the novel signal transduction kinase polypeptide in body fluids or tissue and cell extracts.

Diagnostic assays using the human signal-transduction polypeptide specific antibodies are useful for the diagnosis of conditions, disorders or diseases characterized by abnormal expression of the receptor tyrosine kinase or expression of genes associated with abnormal cell growth. Diagnostic assays for the signal-transduction kinase of this invention include methods utilizing the antibody and a label to detect the human kinase polypeptide in human body fluids, cells, tissues or sections or extracts of such tissues. The polypeptides and antibodies of the present invention may be used with or without modification. Frequently, the polypeptides and antibodies will be labeled by joining them, either covalently or noncovalently, with a reporter molecule, a myriad of which are well-known to those skilled in the art.

A variety of protocols for measuring the kinase polypeptide, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on the human signal-transduction kinase polypeptide is preferred, but a competitive binding assay may be employed. These assays are described, among other places, in Maddox, D. E. et al., J. Exp. Med. 158:1211 (1983); Sites, D. P., et al., *Basic and Clinical Immunology*, Ch.22, 4th Ed., Lange Medical Publications, Los Altos, Calif. (1982); U.S. Pat. Nos. 3,654, 090, 3,850,752; and 4,016,043.

In order to provide a basis for the diagnosis of disease, normal or standard values for the tyrosine kinase, normal expression levels must be established. This is accomplished by combining body fluids or cell extracts taken from normal subjects, either animal or human, with antibody to the human kinase polypeptide under conditions suitable for complex formation which are well known in the art. The amount of standard complex formation may be quantified by comparing it with a dilution series of positive controls where a known amount of antibody is combined with known concentrations of purified tyrosine kinase polypeptide. Then, standard values obtained from normal samples may be compared with values obtained from samples from subjects potentially affected by a disorder or disease related to the human tyrosine kinase expression. Deviation between standard and subject values establishes the presence of the disease state.

Kits containing a corresponding tyrosine kinase nucleic acid or antibodies to a corresponding polypeptide, or protein, e.g., SEQ ID NO:3 may be prepared. Such kits are used to detect heterologous nucleic acid which hybridizes to the nucleic acid or may be amplified via PCR, or to detect the presence of protein or peptide fragments in a sample. Such characterization is useful for a variety of purposes including, but not limited to, diagnosis of pathophysiological conditions, forensic analyses, and epidemiological studies.

The DNA molecules, RNA molecules, recombinant protein and antibodies of the present invention may be used to screen and measure levels of the novel kinase DNA, RNA or protein. The recombinant proteins, DNA molecules, RNA molecules and antibodies lend themselves to the formulation of kits suitable for the detection and typing of the signal-transduction tyrosine kinase. Such a kit comprises a compartmentalized carrier suitable to hold in close confinement at least one container. The carrier would further comprise reagents such as recombinant kinase or anti-kinase antibodies suitable for detecting the novel molecule as depicted in SEQ ID NO:3. The carrier may also contain a means for detection such as labeled antigen or enzyme substrates or the like.

Polynucleotide sequences which encode the transduction molecule may be used for the diagnosis of conditions or diseases with which the expression of the novel human stress-activated kinase is associated. For example, polynucleotide sequences encoding the signal-transduction molecule may be used in hybridization or PCR assays of fluids or tissues from biopsies to detect expression of the kinase. The form of such qualitative or quantitative methods may include Southern or northern analysis, dot blot or other membrane-based technologies; PCR technologies; dip stick, pin, chip and ELISA technologies. All of these techniques are well known in the art and are the basis of many commercially available diagnostic kits. Such assays may also be used to evaluate the efficacy of a particular therapeutic treatment regime in animal studies, in clinical trials, or in monitoring the treatment of an individual patient. Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

Polynucleotide sequences which encode the novel kinase may also be employed in analyses to map chromosomal locations, e.g., screening for functional association with disease markers. Moreover the sequences described herein are contemplated for use to identify human sequence polymorphisms and possible association with disease as well as analyses to select optimal sequence from among possible polymorphic sequences for the design of compounds to modulate the biological and/or pharmacological activity. Furthermore the sequences are contemplated as screening tools for use in the identification of appropriate human subjects and patients for therapeutic clinical trials.

PCR Diagnostics

The nucleic acid sequence, oligonucleotides, fragments, portions or antisense molecules thereof, may be used in diagnostic assays of body fluids or biopsied tissues to detect the expression level of the novel human signal-transduction kinase molecule. For example, sequences designed from the cDNA sequence SEQ ID NO:1 or sequences comprised in SEQ ID NO:2 can be used to detect the presence of the mRNA transcripts in a patient or to monitor the modulation of transcripts during treatment. Several examples of PCR primers derived from SEQ ID NO:1 are set forth herein.

Diagnostic or compositions for pharmacogenomic analysis are preferred for the identification of a polynucleotide sequence comprising PCR primers derived from SEQ ID NO:1 or allele sequences described herein representative of 11, 12, 13 or 15 GT repeats between positions 2125 and 2152 of SEQ ID NO:1.

One method for amplification of target nucleic acids, or for later analysis by hybridization assays, is known as the polymerase chain reaction ("PCR") or PCR technique. The PCR technique can be applied to detect sequences of the invention in suspected samples using oligonucleotide primers spaced apart from each other and based on the genetic sequence, e.g., SEQ ID NO:1, set forth herein. The primers are complementary to opposite strands of a double stranded DNA molecule and are typically separated by from about 50 to 450 nucleotides or more (usually not more than 2000 nucleotides). This method entails preparing the specific oligonucleotide primers followed by repeated cycles of target DNA denaturation, primer binding, and extension with a DNA polymerase to obtain DNA fragments of the expected length based on the primer spacing. One example embodiment of the present invention is a diagnostic composition for the identification of a polynucleotide sequence comprising the sequence as depicted in SEQ ID NO:2 comprising PCR primers derived from SEQ ID NO:1. The degree of amplification of a target sequence is controlled by the number of cycles that are performed and is theoretically calculated by the simple formula 2n where n is the number of cycles. See, e.g., Perkin Elmer, PCR Bibliography, Roche Molecular Systems, Branchburg, N.J.; CLONTECH products, Palo Alto, Calif.; U.S. Pat. No. 5,629,158, Solid Phase Diagnosis of Medical Conditions, issued May 13, 1997.

Compositions

Pharmaceutically useful therapeutic compositions which comprise a nucleic acid coding region, a dominant negative mutant coding region, an antisense molecule described herein, a polypeptide as depicted in SEQ ID NO:3 or a variation thereof contemplated herein, or a compound that modulates the biological and/or pharmacological activity of the signal transduction biomolecule set forth herein may be formulated according to known methods such as by the admixture of a pharmaceutically acceptable carrier. Examples of such carriers and methods of formulation may be found in *Remington's Pharmaceutical Sciences* (Maack Publishing Co, Easton, Pa.). To form a pharmaceutically acceptable composition suitable for effective administration, such compositions will contain an effective amount of the protein, DNA, RNA, or modulator.

Therapeutic or diagnostic compositions of the invention are administered to an individual or used in amounts sufficient to treat or diagnose disorders related to or mediated by the receptor tyrosine kinase described herein. The effective amount may vary according to a variety of factors such as the individual's condition, weight, sex and age. Other factors include the mode of administration.

The term functional derivative includes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as *Remington's Pharmaceutical Sciences*.

Pharmaceutical compositions suitable for use in the present invention include compositions wherein the active ingredients are contained in an effective amount to achieve the intended purpose. The determination of an effective dose is well within the capability of those skilled in the art. The therapeutically effective dose can be estimated initially either in cell culture assays, e.g., of neoplastic cells, or in animal models, usually mice, rabbits, dogs, or pigs. The animal model is also used to achieve a desirable concentration range and route of administration. Such information can then be used to determine useful doses and routes for administration in humans. A therapeutically effective dose refers to that amount of compound, protein, peptide, nucleic acid, antibodies, antagonists, or inhibitors which ameliorate the symptoms or condition. The exact dosage is chosen by the individual physician in view of the patient to be treated.

Compounds identified according to the methods disclosed herein may be used alone at appropriate dosages defined by routine testing in order to obtain optimal modulation of a signal-transduction tyrosine kinase, or its activity while minimizing any potential toxicity. In addition, co-administration or sequential administration of other agents may be desirable.

The pharmaceutical compositions may be provided to the individual by a variety of routes such as subcutaneous, topical, oral and intramuscular. Administration of pharmaceutical compositions is accomplished orally or parenterally. Methods of parenteral delivery include topical, intra-arterial (directly to the tissue), intramuscular, subcutaneous, intramedullary, intrathecal, intraventricular, intravenous, intraperitoneal, or intranasal administration. The present invention also has the objective of providing suitable topical, oral, systemic and parenteral pharmaceutical formulations for use in the novel methods of treatment of the present invention. The compositions containing compounds identified according to this invention as the active ingredient for use in the modulation of a signal-transduction molecule can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as a signal-transduction tyrosine kinase modulating agent.

The daily dosage of the products may be varied over a wide range from 0.01 to 1,000 mg per adult human/per day. For oral administration, the compositions are preferably provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 100 mg/kg of body weight per day. The range is more particularly from about 0.001 mg/kg to 10 mg/kg of body weight per day. Even more particularly, the range varies from about 0.05 to about 1 mg/kg. Of course the dosage level will vary depending upon the potency of the particular compound. Certain compounds will be more potent than others. In addition, the dosage level will vary depending upon the bioavailability of the compound. The more bioavailable and potent the compound, the less compound will need to be administered through any delivery route, including but not limited to oral delivery. The dosages of the human signal-transduction kinase modulators are adjusted when combined to achieve desired effects. On the other hand, dosages of these various agents may be independently optimized and combined to achieve a synergistic result wherein the pathology is reduced more than it would be if either agent were used alone. Those skilled in the art will employ different formulations for nucleotides than for proteins or their inhibitors. Similarly, delivery of polynucleotides or polypeptides will be specific to particular cells and conditions.

EXAMPLES

Example I

Production and Purification of GST-fusion Protein Containing the Novel Human Signal Transduction Tyrosine Kinase Polypeptide The cDNA (SEQ ID NO:1) which encodes the novel human signal transduction tyrosine kinase (SEQ ID NO:3) may be produced using the primers:

1. 5'-GCCGTCGACTGTGGGCCTAGCAGGGAA-3'  (SEQ ID NO:5)

2. 5'-GCCGCGGCCGCTCAAAGCATGCTATAG-3'  (SEQ ID NO:6)

The PCR product is cloned into the Sal I and Not I restriction enzyme sites in the pGEX-5X-3 vector (PHARMACIA BIOTECH, Piscataway, N.J.).

A single colony of DH5alpha (LIFE TECHNOLOGIES, Gaithersburg, Md.) expressingGST fused to the novel tyrosine kinase with and without the transmembrane region is inoculated in 10 ml of LB/amp (100 μg/ml) for overnight culture with a rotation of 275 rpm at 37° C. Next day, the O/N culture is diluted to 100 ml in LB/amp and grown for an hour. IPTG is added to 0.5 mM and grown for additional 3 hrs. The rest of the steps are done at 4° C. Bacteria is harvested by spinning at 5000 rpm for 5 min and re-suspended in 15 ml lysis buffer containing 50 mM Tris (pH 8.0), 150 mM NaCl, 0.5% Triton X-100, 1 mM PMSF and Complete Protease Inhibitor Cocktail. Cells are lysed by sonicating on ice. The Lysed cells are centrifuged and the supernatant containing fusion proteins is collected. The GST-fusion protein is purified using 150 μl of packed beads of Glutathione-Sepharose 4B beads. Beads are incubated with cell lysate for 1 hr and the beads are washed 5x with 50 mM Tris (pH 8.0), 150 mM NaCl, 0.1% Triton X-100, 1 mM PMSF and Complete Protease Inhibitor Cocktail. The washed beads are kept at 4° C., as a 2% suspension in the same buffer with 0.02% azide.

Example II

Demonstration of a Variable Number of GT Repeats in the Tyrosine Kinase Gene

To determine allele frequency of the tyrosine kinase in humans, positions 2062–2083 of SEQ ID NO:1 (forward primer) and positions 2239–2250 of SEQ ID NO:1 (reverse primer) were used in PCR amplification of this fragment of genomic DNA from 27 unrelated Caucasians. The reverse oligo was modified to include the M13F sequence (Vieira, J. and Messing, J., Methods in Enzymol., 153:3 (1987)) at its 5'end. The PCR products were sequenced by dye-primer sequencing (Martin, et al., Bio/Technology, 3:911 (1985) using an M13F primer.

The number of CA/GT repeats between positions 2125 and 2152 corresponding to SEQ ID NO:1 were counted. SEQ ID NO:1 as listed herein demonstrates a total of 14 GT repeat sequences between positions 2125 and 2152. DNA sequencing of the PCR fragments showed 11,12,13,14 and 15 copies of the GT repeat in the genomic DNA of the Novel tyrosine kinase gene from 27 caucasians with the following frequencies:

| Allele | Frequency |
|---|---|
| 11 | 6/54 |
| 12 | 2/54 |
| 13 | 17/54 |
| 14 | 16/54 |
| 15 | 13/54 |

No homozygotes were observed for any allele. Each of the alleles are intended to be within the scope of the claims appended hereto (SEQ ID NO:1).

Example III

Antisense Oligonucleotides Derived from SEQ ID NO:1 Inhibit Proliferation of A549 Cells Oligonucleotides are added to A549 cells at 2 μM concentration using the following experimental conditions. A549 cells are seeded at a concentration of 3000 cells per well in a 96 well culture plate. The cells are incubated overnight before transfection. The medium is aspirated, and the cells are washed once with 150 μl Opti-MEM. Subsequently, 70 μl Opti-MEM containing 30 μl Lipofectin/ml Opti-MEM per 2 μM oligo is used. The cells are incubated with the selected oligomer for 3–6 hours at 37° C. with 5% CO2. After that incubation 70 μl complete medium containing 2×FBS is added into each well. Cell proliferation is measured 20 hours after transfection using One Solution Cell Proliferation Assay Kit from Promega. Briefly, 28 μl of One Solution Reagent is added into each well and the plates are incubated for 2 hours at 37° C. in a humidified, 5% CO2 atmosphere. After the 2 h incubation, the absorbance is measured at 490 nm.

Example IV

Immunoprecipitation

Experiments demonstrate the presence of the novel human signal transduction tyrosine kinase. Human lung carcinoma cell line (A549) was lysed in lysis buffer containing 50 mM Tris (pH8.0), 150 mM NaCl, 0.5% Triton X-100, 1 mM PMSF and Complete Protease Inhibitor Cocktail. All the steps were carried at 4° C. Cell lysates from approximately 2.5×10$^6$ lung carcinoma cells were incubated with 10 μl of rabbit polyclonal antiserum for 2 hrs with continuous rotation. Preimmune serum from the same rabbit was used as a negative control. Immune complexes were captured by the addition of Protein A sepharose beads (Pharmacia) and rocking for additional 1 hr. The beads were washed 5 times in lysis buffer. The bound protein was eluted in sample buffer and subjected to SDS-PAGE on a 8% gel.

Example V

Assay for Kinase Activity

Recombinant, purified GST/SEQ ID NO:3 kinase (or other recombinant protein derived from SEQ ID NO:3) is added to 20 μg enolase in 10 μL of a 3×kinase reaction buffer (KRB) containing (in mM): 60 HEPES (pH 7.5), 30 magnesium acetate, 0.15 ATP, 3 DTT, 0.03 sodium orthovanadate. The reaction is started by the addition of 5 μCi [γ-$^{32}$P] ATP (10 μL). Samples are incubated for 5 minutes at 30° C. The reaction stopped by addition of 4×Laemmli sample buffer. Proteins are separated on 12% Tris/glycine SDS gels, stained with Coomassie blue, dried and exposed to autoradiograph film.

Example VI

High Throughput Screening for Compounds which Modulate Activity

High throughput screening for modulator compounds is performed using enolase coated 96-well FlashPlates® (NEN™ Life Science Products). Kinase reaction buffer (3×kinase reaction buffer (KRB) contains: 60 mM HEPES (pH 7.5), 30 mM magnesium acetate, 0.15 mM ATP, 3 mM DTT, 0.03 mM sodium orthovanadate) 0.25 μCi [γ$^{33}$P]-ATp at a concentration no greater than 1 μg/ml, (determined by titration of individual enzyme preparations for a concentration that allows kinetic determinations over a 1 hour time course of the tyrosine kinase) are added to each well and incubated 1 hour at 30° C. in the presence or absence of 10 μM test compound. Total reaction volume is 100 μL. Following incubation, the reaction mixture is aspirated and the wells rinsed 2 times with 300 μL PBS. Incorporation of radiolabeled phosphate is determined by scintillation counting, Packard Instrument Co.TopCount, 12-detector, 96-well microplate scintillation counter and luminescence counter, model B991200. Compounds which inhibit kinase activity ≧50 percent at 10 μm are indicated by a >50% reduction in scintillation counts. Specificity and selectivity are determined by titration of inhibitory compounds to determine the IC$_{50}$ (or other standard quantitation well known in the art for comparison) and by the substitution of other kinases in the assay. For example, determination of relative inhibitory activity of kinases in comparison to recombinant SEQ ID NO:3 expressed and isolated in a similar manner, assayed under similar conditions, provides selectivity data. Cooper, et al., J. Biol. Chem., 259:7835 (1984). Phosphorylation sites in enolase are utilized by tyrosine protein kinases in vivo and in vitro.

Alternatively, a filter assay may be used. This protocol is the same but the reaction is stopped by the addition of EDTA (pH 7.0) to a final concentration of 80 mM. Samples are then centrifuged and 50 μL of the supernatant spotted on p81 cation-exchange filter paper (Whatman, No. 3698 915). The filters are then washed 3 times in 200 mL of 180 mM H$_3$PO$_4$ (5–10 min each) and once in 200 mL of 96% ethanol. After air drying the filters, radioactivity is determined by Cerenkov counting in a scintillation counter.

Example VII

Efficacy in Vivo (Pharmacological Activity) Screen

To further evaluate the ability of a compound to inhibit human tumor growth, for example, human tumor cells are injected into SCID mice (severe combined immunodeficiency) to form palpable tumor masses. The effects of various doses (e.g., 0.5–50 mg) of a compound in inhibiting tumor growth can be determined as follows: approximately 1×10$^7$cells of the CCL 221 cell line (ATCC, Rockville, Md.), a human colon adenocarcinoma cell line, is suspended in 100 μl DMEM and injected subcutaneously into SCID mice, such that two tumors per mouse are formed. SCID mice receive CCL 221 cells and the tumors are grown for 7 days without treatment; on the 7th day (Day 0) tumor maximal diameters and animal weights are recorded and the mean tumor size for the mice is determined. On Day 1 (eight days following tumor cell injection), treatment of the mice with the candidate compound or vehicle alone is begun. One group of the mice (controls) are injected intraperitoneally with 0.2 ml of vehicle and a second group of mice receives compound by intraperitoneal injection. Various doses (0.25–75 mg) of the compound can be tested in separate groups of mice. On Day 7 and Day 14, animal weight and maximal tumor diameter is measured. Average maximal tumor size for each group on Day 0, Day 7, and Day 14 are compared Day 14, one high dose animal is followed for an additional to determine whether the agent produces a dose-dependent inhibition of tumor growth. Toxicity effects can be examined by tracking mice weight and by harvesting lungs, livers, and spleens of the animals for histological staining.

All publications and patents mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A purified polynucleotide comprising a nucleic acid sequence which encodes a polypeptide selected from the group consisting of: SEQ ID NO:3, SEQ ID NO:3 positions 1–25, SEQ ID NO:3 positions 1–122, SEQ ID NO:3 positions 26–422, and SEQ ID NO:3 positions 123–422.

2. An expression vector comprising the polynucleotide of claim 1.

3. A host cell, said host cell in culture comprising the expression vector of claim 2.

4. A method for producing a polypeptide selected from the group consisting or SEQ ID NO:3, SEQ ID NO:3 positions 1–25, SEQ ID NO:3 positions 1–122, SEQ ID NO:3 positions 26–422, and SEQ ID NO:3 positions 123–422, said method comprising the steps of:

a) culturing the host cell of claim 24 under conditions suitable for the expression of said polypeptide, and b) recovering said polypeptide from the host cell culture.

* * * * *